United States Patent
Lee et al.

(10) Patent No.: US 8,954,145 B2
(45) Date of Patent: Feb. 10, 2015

(54) ANIMAL AND PLANT CELL ELECTRIC STIMULATOR WITH RANDOMIZED SPATIAL DISTRIBUTION OF ELECTRODES FOR BOTH CURRENT INJECTION AND FOR ELECTRIC FIELD SHAPING

(76) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 13/470,275

(22) Filed: May 12, 2012

(65) Prior Publication Data

US 2012/0289823 A1 Nov. 15, 2012

Related U.S. Application Data

(60) Provisional application No. 61/486,179, filed on May 13, 2011.

(30) Foreign Application Priority Data

May 11, 2012 (EP) .................................... 12167688

(51) Int. Cl.
*A61N 1/362* (2006.01)
*A61N 1/05* (2006.01)
*A61N 1/02* (2006.01)
*A61N 1/36* (2006.01)
*A61N 1/368* (2006.01)

(52) U.S. Cl.
CPC ............. *A61N 1/0534* (2013.01); *A61N 1/025* (2013.01); *A61N 1/0565* (2013.01); *A61N 1/36185* (2013.01); *A61N 1/3686* (2013.01); *A61N 1/36067* (2013.01)
USPC ............................................................ 607/9

(58) Field of Classification Search
USPC .................... 607/9, 2, 45, 116, 117, 118, 119
See application file for complete search history.

(56) References Cited

U.S. PATENT DOCUMENTS

| | | | |
|---|---|---|---|
| 2003/0114886 A1* | 6/2003 | Gluckman et al. ................. | 607/2 |
| 2009/0043346 A1* | 2/2009 | Palti et al. .......................... | 607/2 |
| 2012/0046715 A1* | 2/2012 | Moffitt et al. ..................... | 607/59 |
| 2012/0103653 A1* | 5/2012 | Frenzel et al. ................. | 174/108 |

OTHER PUBLICATIONS

Collen Clancy and Yang Xiang "Wrapped aroung the heart", Nature Mar. 6, 2014.
Lizhi Xu et al. "3D multifunctional integumentary membranes for spatiotemporal cardiac measurements and stimulation across the entire epicardium", Nature Communications Feb. 25, 2014.
Hubert C. F. Martens "Spatial steering of deep brain stimulation volumes using a novel lead design", Clinical Neurophysiology vol. 122, pp. 558-566 (2011).

* cited by examiner

*Primary Examiner* — Christopher D Koharski
*Assistant Examiner* — Frances Oropeza

(57) ABSTRACT

An electric stimulator for heart, brain, organs and general cells with a random shape and position of electrodes which enhances its performance for breaking the symmetry. Two types of electrodes are introduced: type-1, or active electrodes are similar to prior art, while type-2, or passive electrodes have not been used in this context. Passive electrodes are electrically insulated, being unable to inject current in the surrounding medium, but they are capable of shaping the electric field, which has consequence on the path of the stimulating currents injected by type-1 electrodes.

21 Claims, 17 Drawing Sheets

1 mm.

1 mm.

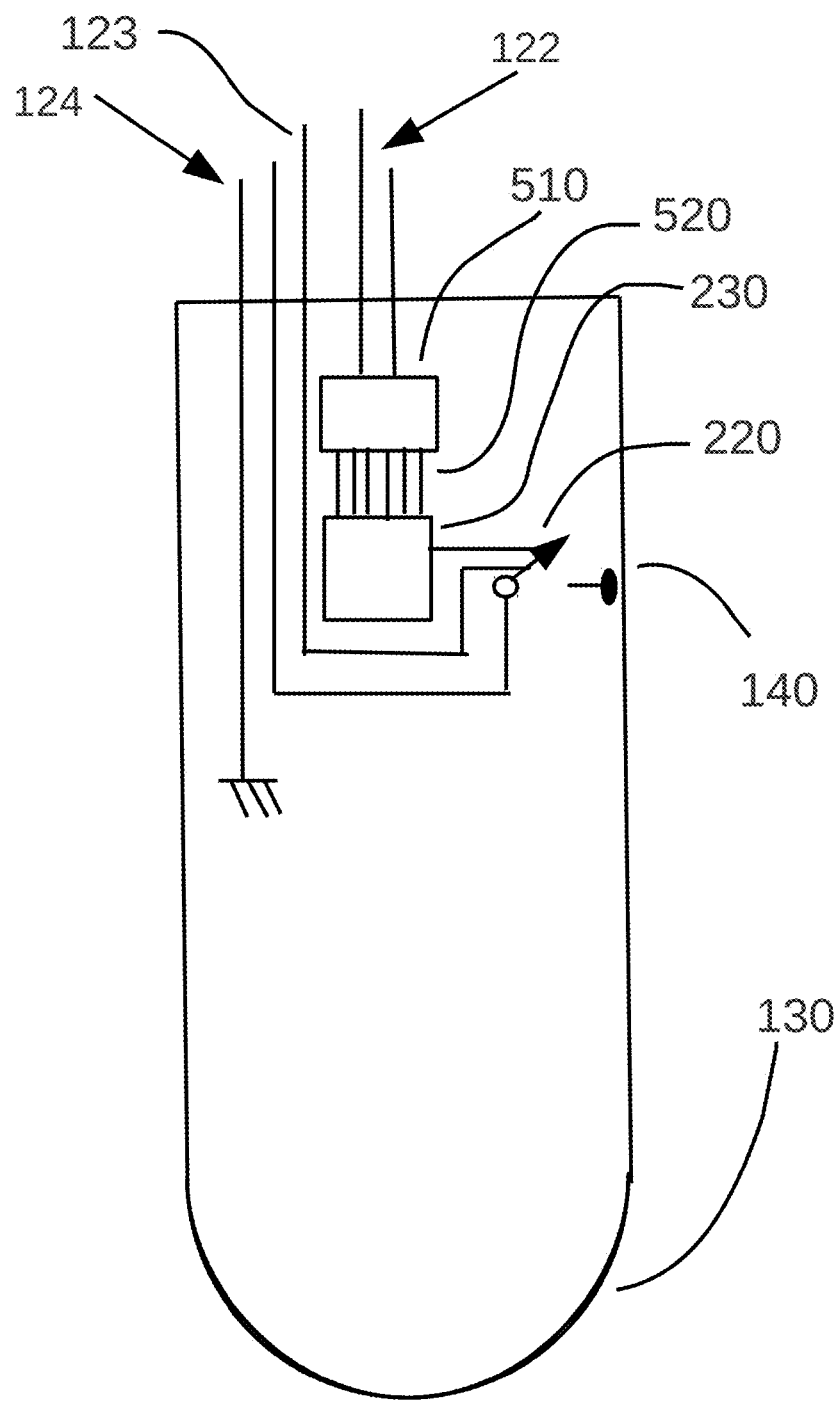

ANIMAL AND PLANT CELL ELECTRIC STIMULATOR WITH RANDOMIZED SPATIAL DISTRIBUTION OF ELECTRODES FOR BOTH CURRENT INJECTION AND FOR ELECTRIC FIELD SHAPING

CROSS-REFERENCE TO RELATED APPLICATIONS

This application claims priority to U.S. Provisional Patent Application No. 61/486,179 dated 13 May 2011, entitled "Cell electric stimulator with randomized spatial distribution of electrodes for both current injection and for field shaping", which is incorporated herein by reference in its entirely.

This application is related to U.S. patent publication number 20100082076, entitled "Method and means for connecting and controlling a large number of contacts for electrical cell stimulation in living organisms" by Chong Il Lee and Sergio Monteiro, published Apr. $1^{st}$, 2010, now issued U.S. Pat. No. 8,565,868 which is incorporated herein by reference in its entirety.

This application is related to U.S. patent publication number 20100079156, entitled "Method and means for connecting a large number of electrodes to a measuring device" by Chong Il Lee and Sergio Monteiro, published Apr. $1^{st}$, 2010, now issued U.S. Pat. No. 8,335,551, which is incorporated herein by reference in its entirety.

This application is related to U.S. patent application Ser. No. 13/053,137, dated Mar. 21, 2011 entitled "Method and means to address and make use of multiple electrodes for measurements and electrical stimulation in neurons and other cells including brain and heart" by Chong Il Lee and Sergio Monteiro, currently issued on Sep. 17, 2013, U.S. Pat. No. 8,538,516 which is incorporated herein by reference in its entirety.

BACKGROUND OF THE INVENTION

1. Field of Invention

This invention relates to electrical stimulation of cells in animals and other living forms, particularly to electrical stimulation of heart cells, including heart muscles associated with heart muscle contraction and purkinje and similar fibers, and more precisely, it relates to the art of causing an efficient contraction sequence of the heart muscle in order to maximize the volume of blood pumped per unit of energy spent by the heart. It also relates to the art of electrical stimulation of neurons as in brain and peripheral neurons. Brain neurons are stimulated both for clinical objectives, as in Parkinson's disease control, and in animal research as well, in which case neurons are stimulated to observe the consequences of the stimulation.

2. Discussion of Prior Art

The heart is divided into four chambers: left and right atria, at the upper part of the heart, and left and right ventricles, at the lower part of the heart. Right and left are conventionally assigned to be from the point of view of the person—which is the opposite left-right from the point of view of the observer looking at the person from the front. The atria are more holding chambers then actually pumping devices, evolved to quickly fill up the ventricles, below them, and consequently their walls are thinner when compared with the lower part, the ventricles. The right heart is responsible for the pulmonary circulation, receiving venous (non- or little-oxygenated) blood from the full body at the right atrium, passing it down to the right ventricle below it, from where the blood is pumped to the lungs. This corresponds to a short path, to the lungs and back. Back from the lungs, the blood enters the left atrium, which holds some oxygenated blood volume then releases it down to the left ventricle below it, from where the blood is then pumped to the whole body. The left heart pumps blood to the whole body, which involves more work when compared with the shorter path from the right heart to lungs and back, so the left atrium has thicker, stronger walls. These considerations on the wall thickness are of importance on our invention, because our invention deals with the optimization of the pumping mechanism of the heart, which is heavily dependent on the propagation delays of the electrical pulses that causes the pumping mechanism, as explained below.

The electrical nature of muscle contraction was first observed in the waning years of the 1700s by Luigi Galvani, who noticed that a frog's leg contracted when subjected to an electric current. Today it is known that all our muscles, from a blinking eye to a walking leg, work on the same principles observed by Galvani—including out heart. The heart contracts as response to an electric pulse, which is injected on it at the required frequency, which varies according to the person's activity and state of excitation. It is crucial here to keep in mind that this electric pulse does not propagate as the ordinary power in copper wires, which occurs very fast, virtually instantaneously, but propagates rather as a displacement of heavy ions inside and outside of the muscle cells, subjected to much scattering and other obstacles. In fact, the time elapsed between the initial contraction of the atrium, or upper heart chamber, and the ventricle, or lower heart chamber, is of the order of 120 to 200 ms—a rather long time for electronics events (long enough for an electric pulse on a power line to go completely around the earth. This slow propagation of the electrical pulse in the heart muscle is important for the working of our invention, so the reader is requested to keep this in mind.

Several malfunctions are possible to occur that hinder the proper functioning of the heart. Some are of a mechanical nature, a subject not bearing on our invention, while some are of an electrical nature, which is the focus of our invention, as described later on: our invention is an inventive method and means to cause a better propagation of the electric pulse that causes the heart to beat.

Given that a proper understanding of the mechanism of heart beating and of the propagation of the electrical pulse that determines it is crucial to the understanding of our invention, we proceed to a brief explanation of the mechanism of the heart beating. This is also necessary because our invention is based on two separated and insulated fields of knowledge: medicine & physiology and electrical engineering, which are separated well understood by two groups of persons, but hardly by the same individual.

There are a wealth of books on the subject, as Thaler (2003), where the reader with a non-medical background can get more detailed information. In short, most muscles capable of contracting are made of such cells that under normal conditions they have an excess of negative ions inside their cellular walls, which causes an excess of positive ions just outside their cellular walls, attracted there by ordinary electrostatic attraction. When in this condition, its normal condition, the cell is said to be polarized. If the cell loses its inner negativity, the language of electrophysiology describes this as a depolarization event. We here warn the reader that this is a poor choice of name, because the cell is still polarized when the electrophysiologists mention a depolarization event, but it becomes polarized on the opposite direction (positive inside it). By a sequence of well-know mechanism this acquisition of positive charges (depolarization as said in the trade, misnomer as it is) causes the cell to contract, that is, to decrease its length. This is the mechanism behind the blinking of our eyes, behind our walking—and also behind the heart contraction. It being an electric phenomenon, this event can be controlled by the injection of the appropriate electrical pulse in the heart muscle. This will be described in the sequel, and our invention bears on a twist on the man-made mechanism (heart pacemaker) designed to cause a heart pumping contraction sequence. Our invention improves on the propagation of the artificial electric pulse that causes a heart contraction (and pumping).

As a last preparation information we want to clarify that the heart pumping mechanism is a modification of a class of pumps called peristaltic pump, which causes the motion of the fluid, or pumping, with a progressive forward squeezing of the container, which forces the fluid forward. The reader is requested to keep this fact in mind as he reads the explanation of our invention, that the hearts functions with a progressive squeezing of its chambers, akin to the milking of a caw, during which process the milker progressively squeezes the caw's tit between its pointing finger and the thumb, then press the middle finger, squeezing the store liquid further down from the tit, then the annular than the little finger, at which point all the can be squeezed is out, the hand is opened to allow more milk to enter the tit and the process is repeated.

In short, most of the heart cells are part of the miocardium, which is a variety of a large group of other cells which are capable of contracting when subjected to the mechanism just described of depolarization. The pumping sequence consists of blood entering the heart at the top of the atrium (which is also the upper chamber), then a sequential downward pumping squeeze of the atrium which squeezes the blood into the lower ventricle. Then there is a problem because the exit of the ventricles is at its upper part, next to the entrance port from the atrium, so, if the squeezing continued downward there would be no place for the blood to go (no exit port at the bottom of the ventricle!). This problem is solved with the interruption of the downward propagating electric pulse at the intersection of these two chambers and a re-emission of another pulse through fast channels known as His fibers, left and right bundles and finally the Purkinjie fibers which release the electrical pulse at the base of the ventricle, which then begin squeezing from bottom to top, squeezing the blood upwards towards the exit port (the pulmonary vein at the right and the aorta at the left).

So, the heart's electrical system starts with an electrical pulse at the top of the right atrium, from a small group of cells known as the sino-atrial node (SA node or SAN), from where it propagates fast to the left atrium by special fibers that propagate the electric pulse better than the miocardio muscle does, which causes a downward contraction of the atrium, the right atrium first, then the left atrium a few milliseconds later. The electric pulse is then captured at the base of the atrium, preventing it from continuing down, it is then used by special cells called the atrial-ventricular node $550avn$ (AV node or AVN) to start a new pulse which is send through special conduits (special wires, so to say), known as the His bundle, then the right and left bundle branch, then the Purkinjie fibers, which then release the electrical pulse regenerated at the atrio-ventricular node $550avn$ at the lower part of the ventricle, causing now the ventricle to start contracting upwards, as needed to pump the blood to the upper exit port of the ventricles. This completes the heart cycle.

Electrical malfunctions of the heart may be more obvious faults as insufficient energy in the electrical pulse that causes the pumping or some more subtle ones as errors in the propagation of the electrical pulse. The original artificial heart pacemakers simply injected an electric pulse near the sino-atrial node SAN at the top of the right atrium, and later versions injected two or even three separate pulses in two or three different parts of the hearts. None of them, though, even attempted to control the path of the injected current once it is injected artificially—which is the object of our invention. In other words, our invention improves on the electrical propagation features of the electric pulse created by the artificial heart pacemakers, and in doing so it improves the squeezing sequence of the heart, which in turn improves the pumping efficiency. It is to be remembered that, because the heart is a variation of a peristaltic pump, the pumping sequence is of fundamental importance for an efficient pumping.

Originally heart pacemakers were simply an exposed wire tip, the wire connected to a battery and electronics circuitry to create pulses of appropriate frequency, shape and amplitude.

The original implant was made with an open chest surgery, but this was quickly supplanted by a less invasive and much less traumatic technique, with which an incision was made on some vein at the chest (usually the subclavian vein, on the upper chest), where a wire was inserted, which had some sort of screwing or anchoring ending at its distal extremity, then this wire was fed in until its distal extremity reached the upper right heart chamber, from the inside (the right atrium), where the wire tip was screwed on the inner part of the heart, near the natural starting point of the electrical pulse that causes the heart to beat, know as the sino-atrial node (SA node or SAN).

The proximal end of the wire was then connected to a battery and electronics box which was implanted in the chest, in some convenient location. From the wire tip anchored at the distal end, a current emanated, which then propagated through the heart muscle, causing the muscle to contract as the current proceeded along it, hopefully similarly to the naturally occurring electric pulse. It is crucial here to remember that this muscle contraction occurs because of the electric charge carried by it, and consequently, it is the electric current propagation time and pathway that determines the heart contraction sequence—because the muscle cells contract as a consequence of the electric charge near it. The sequence of muscle contraction is crucial for an efficient heart functioning, because the heart must start squeezing from its furthest end, away from the discharge exit area, most away from the exit port, continuously squeezing its wall towards the exit port. The heart does not contracts as a person squeezes a tennis ball for exercise, but rather, the heart squeezes sequentially pushing the blood forward, towards the exit port. An example of a similar contraction sequence, for similar objectives, is the milking of a caw, a process which requires that the milker starts squeezing the upper part of the tit, then continue squeezing lower and lower, while keeping the upper part squeezed to prevent the milk to move back, until the end of the tit is squeezed, at which point the milk previously lodged in the tit is moved out and the process starts again. The heart does not squeeze all the blood out of it, as much as the caw milking, cannot squeeze all the milk out of the tit. Most people get astonished when they learn that the heart pumps not much more than 50% of the blood in it—a rather low efficiency!

Over the more than 50 years of heart pacemaking, many types of electrode tips have been developed. Some of the electrode tips possessed some degree of symmetry, some not. Whether or not the tip electrode had or not symmetry, this quality was transferred to the current injected into the heart muscle. The heart, on the other hand, is asymmetric, particularly from the point of view of the point where the stimulating electrode is anchored in the heart, which often is near the sino-atrial node, or at the top of the right atrium. It follows that the current that is injected by current art heart pacemakers cannot follow well the contour of the heart muscle, causing a less than ideal contracting sequence. Other anchoring positions for the electrode are also used, and multiple electrodes as well, which may stimulate the atrium and the ventricle independently In the former case, the tip symmetry had consequences on the current distribution in the heart muscle, because, at least initially, it caused a current symmetry. In the latter case, the lack of symmetry also had consequences on the current distribution, because it caused an initial asymmetric current injection, which could or could not be the ideal for the heart contraction sequence. In either case, the trajectory of current injection has not been controlled by prior art devices, which was a major problem as acknowledged by cardiologists working in the field of electrophysiology. This lack of control of the current distribution, as it propagated through the heart muscle, plagued all the earlier art of heart pacemakers, and still does in current art.

Throughout the years, many variations were introduced in the electrodes, as the shape of the wire tip, which served to anchor it in place, but these changes were largely for mechanical reasons, as to provide a more secure anchoring of the electrode on the heart muscle, or to minimize physical damage to the heart tissues, etc. Changes have also occurred on the method of introducing it in the heart, but most of these were changes to solve other problems, not to induce a good squeezing sequence of the heart muscle. Consequently, the uncontrolled propagation of the electric current from the tip has been a constant. Attempts to improve the electric pulse propagation include the use of multiple wire tips, which injected current not only at different locations but also at different times, or with relative time delay between the stimulating places. Examples of such multiple site stimulation are atrial and ventricular stimulators, two tips, one at the atrium, another at the ventricle, which deliver a pulse with a time lag between them, corresponding to the time lag between atrial contraction and ventricular contraction. But these multiple stimulating tips are not designed to control the electric field— which determines the path of the injected electric current, which follows the electric field lines because these are the force lines.

Such multiple electrodes, usually, though not consistently, worked better than a single electrode. Yet, this lack of optimization of the heart muscle contraction has been a major problem known to the practitioners of the art. This uncontrolled propagation was shared by most, if not all models and their variations, in spite of the fact that the cardiologists were aware that uncontrolled electric pulse propagation caused inefficient heart pumping. Cardiologists knew that they had to address the problem of electric pulse propagation through the heart, but they have so far not succeeded in this goal. It has been a known problem in heart pacemakers, yet and amazingly, a problem which has defied solution for decades.

Moreover, even if multiple stimulating tips caused an improvement of the pumping squeezing sequence and efficiency, it had the detrimental effect of causing more muscle damage, as each anchored wire tip is a foreign body in the heart, also a foreign body which by necessity caused an injure to it, an injury which resulted in a scar tissue, which in turn has different electrical conductivity when compared with the normal heart, creating a problem spot for the very objective of controlled electric pulse propagation. Another problem was that, since often times the first attempt to anchor the tip in the endocardio is unsuccessful, either for mechanical or for electrical reasons, for every unsuccessful attempt the surgeon has to retract the tip then screw it again somewhere else, and occasionally even more than two attempts, each tip were usually responsible for multiple scars in the inner heart, which in turn posed limits to any dream of using a multiplicity of stimulating tips.

It seems that all prior art attempted to solve the problem of electric pulse propagation inside the heart muscle tissues with the use of multiple electrodes, while nobody succeeded to control the current propagation, in direction and magnitude, using one single electrode. Nor have prior art made full use of multiple electrodes to more completely shape the electric field within the heart muscle—which is the same as the electrical current path, because the electric field lines are the same as the force lines, or the lines along which the injected charges move.

Prior art simply used an arbitrarily shaped stimulating electrode, which than created a non-controlled electric field in the surrounding space, which in turn guided the injected charges (or electric current). Our invention offers a method and a means to adjust the electric field, independently from the stimulating electrodes, to the best shape depending on the particular case, as needed.

OBJECTS AND ADVANTAGES

Accordingly, several objects and advantages of our invention are one or more of the following. A better squeezing sequence of the heart muscle, starting the muscle contraction from the distal end of the heart further away from the exit port, to the proximal end of the heart closer to the exit port, with view to achieve a more efficient pumping, when compared with prior art heart pacemakers which were designed with no view to optimize the squeezing sequence.

Another object and advantage of our invention is to offer the ability to inject an electric current in the heart which causes a higher pumping fraction, or the fraction of the blood which is actually pumped out of it, or out of each chamber, when compared with prior art artificial pacemakers.

Another object and advantage of our invention is to adjust the electric field over the heart muscle to take better advantage of the atrial ventricular node to cause a better squeezing sequence of the heart muscle when compared with prior art artificial pacemakers.

Another object and advantage of our invention is to adjust the electric field over the part of the heart muscle where the His bundle and the right and left bundles are, to control the propagation times of the electric current coming from the atrial-ventricular node to the bottom and sides of the ventricle, to cause a better squeezing sequence of the heart muscle when compared with prior art artificial pacemakers.

Another object and advantage of our invention is to control the electric field where the Purkinje fibers are located, to take better advantage of the Purkinje fibers to cause a better squeezing sequence of the heart muscle when compared with prior art artificial pacemakers.

Another object and advantage of our invention are a better volumetric fit of the neural electrical stimulation to the optimal heart and/or other tissues target volume, when compared with current art heart, stimulation devices.

Another object and advantage of our invention is to better control the electric field around the supporting structure from where electrical stimulation is injected in the target volume of the brain when performing Deep Brain Stimulation, to cause that the electrical stimulation reaches a larger volume of the target volume while better avoiding stimulating other parts of the brain that are near but outside and beyond the target volume.

Another object and advantage of our invention is the possibility of time control of stimulation sequences in neural stimulation, which is not achieved with current art devices.

Another object and advantage of our invention is a better control of the shape of the volume of neurons that receive electrical stimulation in brain stimulation, as in DBS (Deep Brain Stimulation)

Another object and advantage of our invention is a better control of the shape of the volume of neurons that receive electrical stimulation in neural stimulation, as for TENS (Tanscutaneous Electrical Neural Stimulation) pain control.

Another object and advantage of our invention is a better control of the shape of the superficial distribution of neurons as for pain control in TENS (Transcutaneous Electrical Neural Stimulation) devices, Another object and advantage of our invention is a better control and shape of the mostly planar electrical stimulation of neurons as used in some cortical brain stimulation.

If one or more of the cited objectives is not achieved in a particular case, any one of the remaining objectives should be considered enough for the patent disclosure to stand, as these objectives and advantages are independent of each other.

Further objects and advantages of my invention will become apparent from a consideration of the drawings, the summary, the description of the invention and its variations, and the claims.

SUMMARY

It is well known in cardiology that the heart pumping efficiency is a direct consequence of a proper propagation, in time and space, through all available electrical paths in the heart cells, of the electrical pulse that causes the heart contraction, including the contraction sequence. This is acknowledged to be true whether the electrical pulse is the natural one starting at the SAN (sino-atrial node) or an artificial one, starting at the anchoring position of an artificial heart pacemaker. It is interesting to note that if evolution have developed the heart in such a way as to maximize a better contraction sequence, starting from an initial electrical pulse at the sino-atrial node (SAN), the pulse initiating from an implanted pacemaker starts at another location, and therefore it can hardly be expected to function the same way as the natural pacemaker at the SAN. It would be expectable that an asymmetric pacemaker would best substitute the natural pacemaker, when located at another position than the natural one. Consequently, the medical profession has been looking for a heart pacemaker that could maximize the pumping efficiency. Such a goal has eluded the practitioners because of a lack of mechanism for precise control of the current injection, in position, direction and relative timing, of the electrical stimulation. Our invention is a step in the direction of better control of this stimulating pulse. Our invention discloses a mechanism to control the magnitude and the direction of the initial current injection in the heart muscle, also time delays between current injected from different locations on the surface of the stimulator; in other words, our invention affords the possibility of controlling the vector current, and the relative time at different directions and places, as opposed to only its magnitude, as in prior art. Our invention also applies to other electrical stimulations as brain (DBS and cortical stimulation), spine, skin, and others.

BRIEF DESCRIPTION OF THE DRAWINGS

FIG. 9 (d and e) Show the effect of changing the numerical value of the electric charges, which is equivalent to modifying the electric potential (or voltage).

FIG. 14 Shows a schematic representation of a brain-type picafina of our invention.

DETAILED DESCRIPTION

Overview

Figure 1:
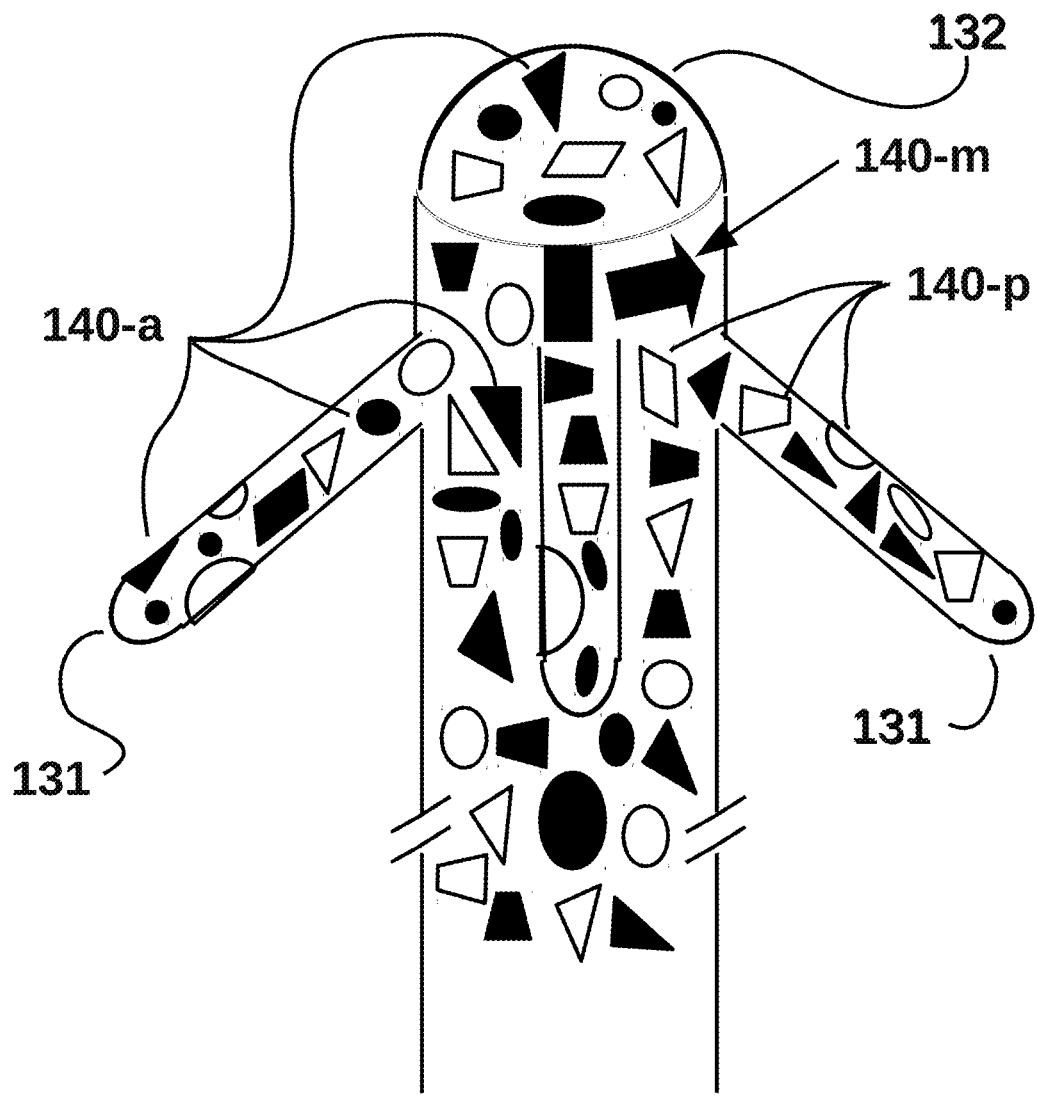
FIG. 1 A heart-type electrical stimulator (heart pacemaker or piquita) with multiple shaped electrodes randomly arranged on its surface.

FIG. 1 shows the main embodiment of our invention, which is for heart pacemaking applications. FIG. 1 is a heart-type electrical stimulator (heart pacemaker or piquita) with multiple shaped electrodes randomly arranged on its surface. Note that similar pattern on different supporting structures are possible, the supporting structure design being determined by its function, as for heart pacemaker (this case), Deep Brain Stimulator (DBS), cortex stimulation, spinal stimulation, stomach stimulation, etc. 140-a points to type1 or active electrodes and 140-p points to type2 or passive electrodes. FIG. 1 shows one of the current art anchoring distal extremities 132 of a current art heart pacemaker with the improvements of our invention. Note that different ending anchoring attachments 131 are in use, and that the model shown in FIG. 1 uses one of the several used attachment endings, but the same principles apply to other anchoring attachments. The main body 132 of the piquita device may have a diameter of 3 mm, and the smaller anchoring side arms 131 may have a diameter of 1 mm. Anchoring arms 131 should have such size and strength enough to keep the tip of the stimulating piquita structure 132 secured in place once it is inserted into the heart muscle. Anchoring arms 131 should prevent the piquita stimulating device from moving back, out or the muscle, this being one of the reasons for its shape and form, resembling a ship's anchor, which has the similar function of holding firm to the sand below the ship. These dimensions may vary without changing the nature of our invention and these values are given as a possible dimension only. On the surface of the main body 132 and of the smaller side arms 131 there are several random-shaped patches which are represented by either a solid black or a white shape represented by its contour. The solid black odd-shaped patches 140-a represent electrodes which we call active, or type-1 electrodes, and the open, odd-shaped patches 140-p represent electrodes which we call passive, or type-II or type-2 electrodes. These are the main inventive character or our invention.

Active, or type-1 electrodes 140-a have a metallic surface which is capable of conducting electricity. Other than their smaller sizes and odd-shapes, they correspond to the prior-art electrodes for electrical stimulation of the heart, from which they only differ in shape and size but otherwise being electrically and functionally similar—though their size and configuration add to their functionality, as explained below. Passive, or type-2 electrodes 140-p also have a metallic surface, but their metallic surface is covered by an insulating layer, which, in the main embodiment is made of silicon oxide. Passive, type-2 electrodes are unable to inject current into the surrounding tissues, but when set at fixed electric potentials (voltages) they do change the shape of the electric field in the neighborhood of the piquita, therefore changing the paths of the injected currents. Passive (type-2) electrodes are incorporated in the piquita for the purpose of field shaping (to change the spatial configuration of the surrounding electric field which in turn changes the path of the electrical stimulation).

Figure 2:
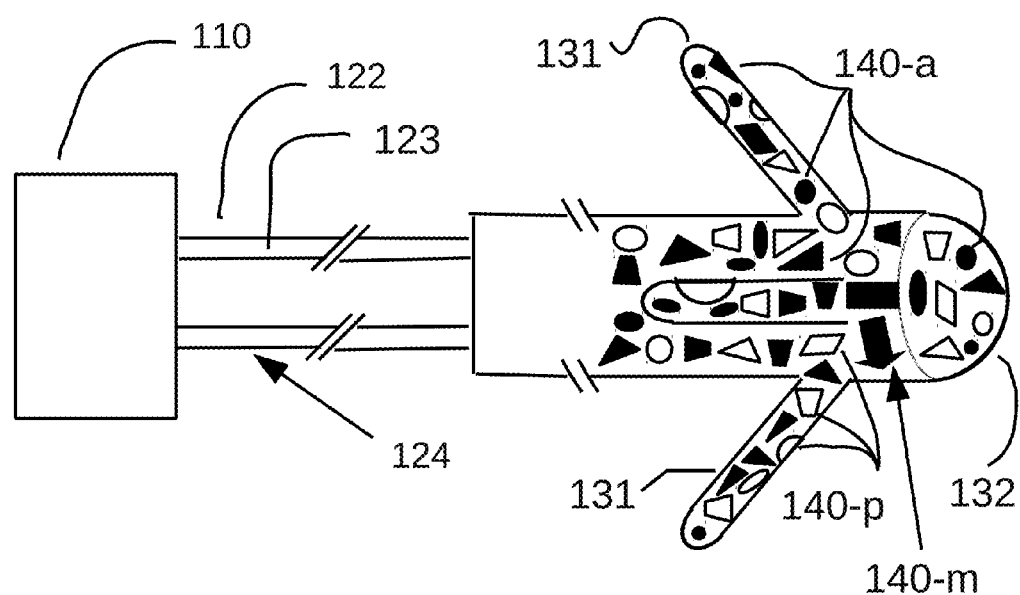
FIG. 2. A heart-type electric pacemaker (piquita) with multiple shaped electrodes connected to the associated battery and electronics.

The reader is here invited to look at FIG. 2 for a schematic representation of a more complete system. FIG. 2 shows a heart-type electric pacemaker (piquita) with multiple shaped electrodes connected to the associated battery and electronics, omitting the details of the electronics both in the battery pack and inside the piquita stimulator itself. To physically achieve the above description, the controlling mechanism, in this case a microcontroller MC1 residing in the battery/control unit BAT1 (FIG. 2), is loaded with a program (or software), which is capable of executing automatic repetitive tasks following a programmed sequence the details of which are adjusted by a medical professional or by the patient himself, which determines a particular combination of active and passive electrodes to use, also able to determine the addresses of which electrodes of each type to use, also able to send this information by wires to the stimulating unit 132. The correct sequence can be determined, for example, by the examination of an EKG (Electro Cardiogram) while varying the active electrodes of each type, their voltages and relative time sequence. The addresses sent by wires by the controlling microprocessor unit MP1 to the stimulating unit 132 to determine which of the electrodes (passive and active) are to be used (turned on) and which electrodes are to be disconnected (turned off)—see FIG. 2. The main embodiment uses a serial bus to send all the information from the controlling unit BAT1 to the stimulating unit 132. An example of a serial bus is a USB, but our invention work with other types of serial buses as well, including, but not limited to, RS-232, firewire, and others.

Figure 3:
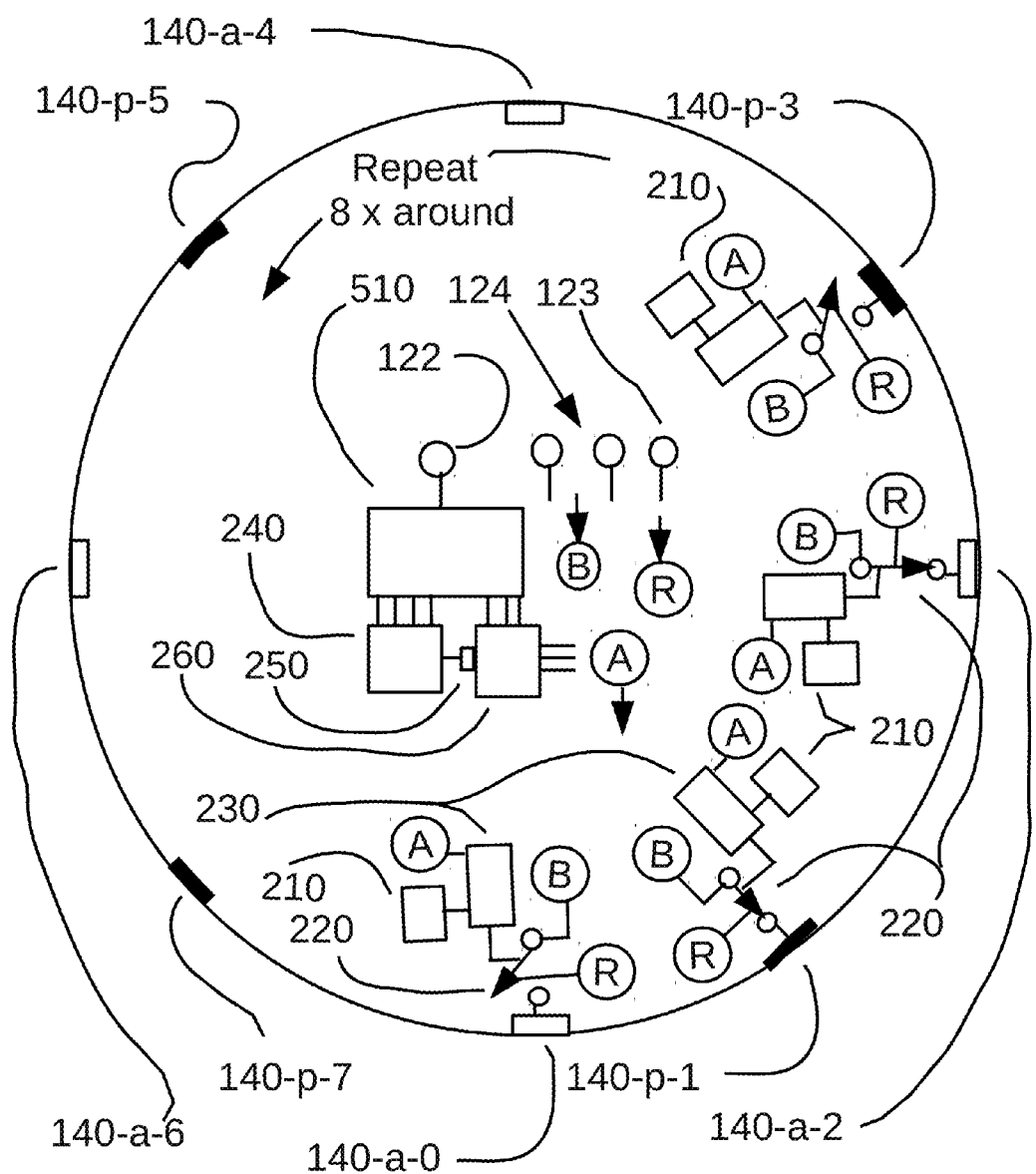
FIG. 3 shows a cross-section of a typical implementation of our invention valid for both the heart (piquita) and the brain (picafina).

Each electrode type can be turned on or off (connected or disconnected from the electrical power) by a switch SW (as seen in FIG. 3) which ending marked B connects to the power carrying means B which runs down the main body 132 of the piquita stimulator which ultimately is connected to the electric energy storage unit by other electrical conductive means, as shown in FIG. 2. FIG. 3 shows a cross-section of a typical implementation of our invention. Several electrodes 140-a (active) and 140-p (passive) are shown. On the surface of the supporting structure, of which FIG. 3 shows a typical cross section, there are many such electrodes possibly spread on a random arrangement. Note that in FIG. 3 both tie heart (piquita) and the brain (ficafina) implementations use similar circuits. The electronics circuits shown are indicated by their main blocks, as these are standard circuits known in prior art to any engineer.

The invention also discloses an important marker to determine the angular position of the piquita with respect to the heart in which it is implanted. FIG. 1 shows one such possible marker: two type-1 active electrode 140-m with such an X-ray opacity (absorption) to be visible during the fluoroscopic images taken during electrode implantation as normally done. Other markers are possible for the same purpose, as the same shapes on type-2 passive electrodes, as side arms 131 of different lengths and/or diameters, or any other asymmetric feature that is visible in some sort of imaging technique, as MRI, X-ray, ultrasound, etc. It is part of our invention that each electrode position and size and orientation is known to the cardiologist (and the computer which he will use to program the device), each electrode being know by a number, as 1, 2, 3, . . . etc., or any other numerical pattern. Marker 140-m allows for the computer program to know the angular position of each electrode, which is needed to determine which individual electrode to connect to which voltage, according to their actual position within the heart muscle, as the piquita happened to have been anchored in it.

Inside the main body 132 and the side arms 131 of the stimulating piquita, there are electrical circuits as displayed in FIG. 3. FIG. 3 is intended as a description of the possibilities for implementing the invention, while not being part of the invention. FIG. 3 schematically shows the electronics, indicated by their main blocks, as these are standard circuits known in prior art to persons familiar with the art of electronics engineering; it is valid for both the piquita (heart implementation) and the picafina (brain implementation) as well. FIG. 3 shows a cross section with the electronics inside. Most of the electronics used to implement our invention is prior art. FIG. 3 is a part of other applied patents of the inventors, e.g., U.S. patent application Ser. No. 12/586,562 ("Method and means for connecting a large number of electrodes to a measuring device"), published 1 Apr., 2010, U.S. patent application Ser. No. 12/586,763 ("Method and means for connecting and controlling a large number of contacts fro electrical cell stimulation in living organisms"), published 1 Apr. 2010, U.S. patent application Ser. No. 13/053,137 ("Method and means to address and make use of multiple electrodes for measurements and electrical stimulation in neurons and other cells including brain and heart"). Alternatively the electronics can be the same, or equivalent of prior art implanted stimulation devices, as Ibrahim, Ibrahim Hanna and Parker, John L., international application number PCT/AU 02/00835, international publication number WO 03/003791 A1, "Multielectrode cochlear implant system with distributed electronics", which is for the similar application of cochlear implant.

As a further example of the electronics needed to implement our invention, in the stimulating unit 132=ST1 there are microelectronics which include serial-to-parallel converters, address comparators, semiconductor switches (or other type of switches) which select which electrodes are on, or connected to power, and which electrodes are off, or disconnected from power (for both type 1 and type 2 electrodes, active and passive electrodes). The selection of electrodes is made with switches controlled by address decoders, each of these address decoders selecting for a particular electrode tip to be turned on. Stimulating unit 132=ST1 is also fitted with all the usual hardware needed for the implementation of the serial data transfer, including clock generation, if the serial transmission uses a USB or a RS-232 type of transfer.

The main embodiment uses 4 electric signal transfer means (may be wires) from the battery pack/control unit BAT1, which are as follows: one wire for the address/control information (serial transfer), one wire for reset, one wire for power, and one wire for return or ground, which is common to both the serial address wire and power. A common ground is possible in this case because the data transfer is so slow that the possibility of capacitive coupling is minimal. This particular choice of 4 wires should not be taken as a limitation on the invention, because more wires or less wires are possible still within the scope of the invention, as obvious to people familiar with the art of electronics. It is also possible to connect the ground (or return) wire to any number of electrodes (or pads), both type 1 and type 2. In the main embodiment the selections latches, that is, once made it keeps the selected state forever, until reset by the reset line. The initial state is, for the main embodiment, all pads (all electrodes) to go to the off, of disconnected state. Other choices are possible still within the scope of the invention, for example, the reset function can be made with a "low", instead of a "high", or the initial state may be any particular combination of "on" and "off" on the available pads or electrodes of each type (active and passive, type 1 and type 2)

Each individual electrode is associated with a unique digital address which is used in the manner described in the sequel, to select which of them is used for electrical stimulation (from the subset that terminates on a conductive tip, or active electrodes), and which are used for field shaping (from the subset that terminates on an insulated tip, non-conductive tip, or passive electrodes), and which are not used at all (disconnected from any electrical energy source).

The random placement, shape and size of the electrodes is a distinct feature of our invention, as it contributes for the creation of a spatial asymmetry of the electrodes, which in turn causes an asymmetry in the spatial distribution of the injected current, either its magnitude or its direction. Careful selection of which electrodes to turn on, and at which electric potentials (voltages) can create the most desirable electric field on the volume of the heart. A careful selection of which electrodes is able to produce a better resulting stimulation which is suited to the asymmetric heart muscle 3-dimensional shape. It is to be noted that if any symmetry is required, our invention is backwards compatible, being able to reproduce old art stimulating surfaces as a particular case of an arbitrary shaped surface. Note that if a symmetry of current magnitude and direction is desired, it can still be achieved within a reasonable accuracy, by the appropriate selection of a number of electrodes which, as a set, defines the desired symmetry.

FIG. 3 shows schematically some of the circuitry that must exist in all the embodiments (heart, brain, etc.) This figure does not show the detail of the circuits because it is part of the old art of electronics digital and analog circuit design, not part of the our invention.

In FIG. 3 there is an serial-to-parallel converter 510, which receives the serial data 122 and converts it to parallel form. Four bits of the paralleled address is decoded by 240 into one of a plurality of planes, and when this 4-bits address matches a particular plane the enable bit 250 is set to enable 260, the 3-bit output A of which then goes to the 8 electrodes of this particular plane (140-a and 140-p). 124 is the power to the electrodes (type-1 and type-2), and 123 is a reset line, which may be used to bring all electrodes to the same initial state, whenever needed, under the control of MP1. 210 is a memory with the local address of each electrode, and 230 is a comparator, which compares the local address 210 with the address from MP1, which appears at A. When these two matches then switch 220 closes (as is the case of 140-p-1), and when these two do not match then switch 220 opens (as is the case of 140-a-0)

Figure 4:
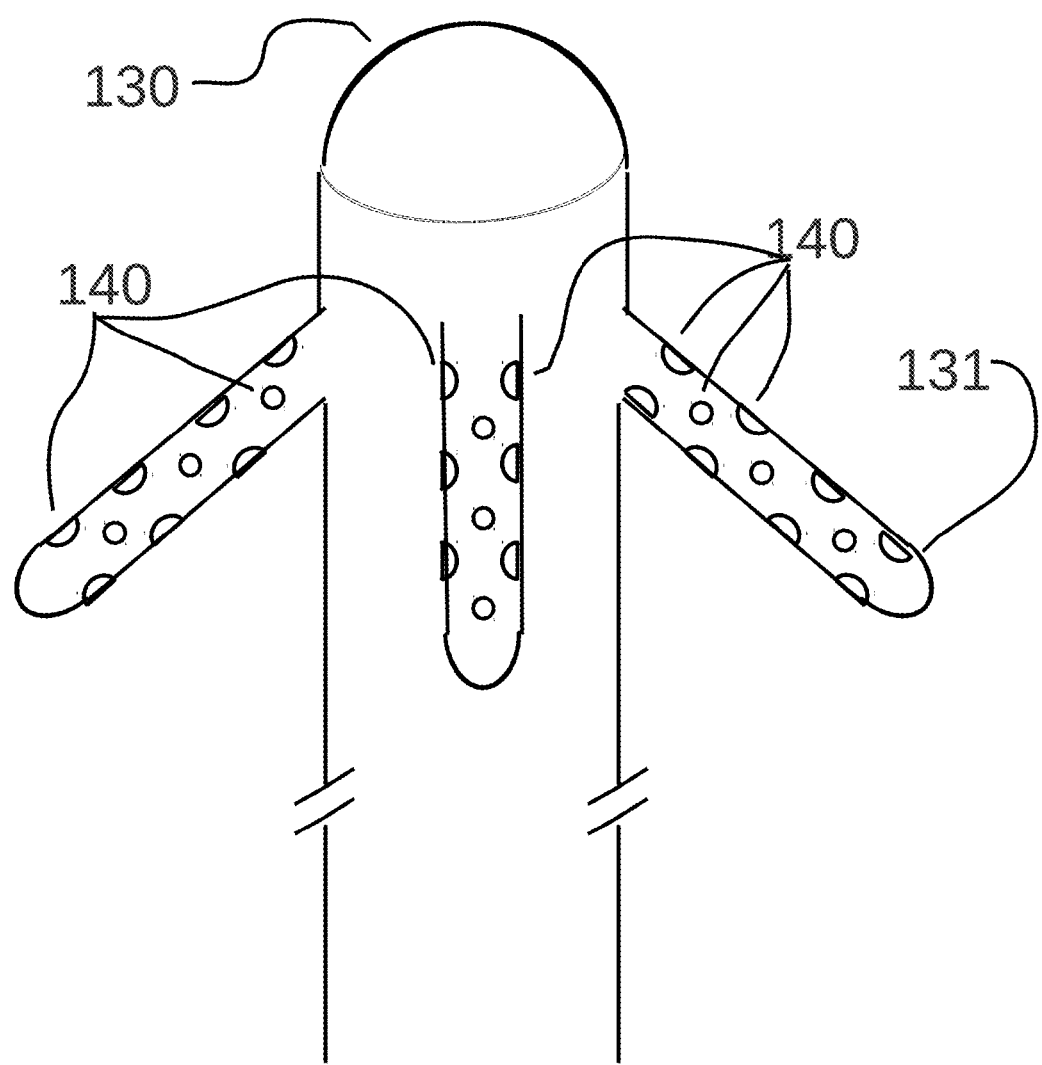
FIG. 4 shows a variation of the heart stimulator piquita.

FIG. 4 shows a variation of the heart-type stimulator piquita with electrodes only at the surface of the side or anchoring arms 131. For simplicity this figure does not differentiate between the two types of electrodes 140-a and 140-p, but it is understood that the general denomination 140 intends for both types of electrodes, either randomly or orderly distributed on the surface of 131.

Operation of Invention

Background Information on Operation of the Invention.

Figure 5:
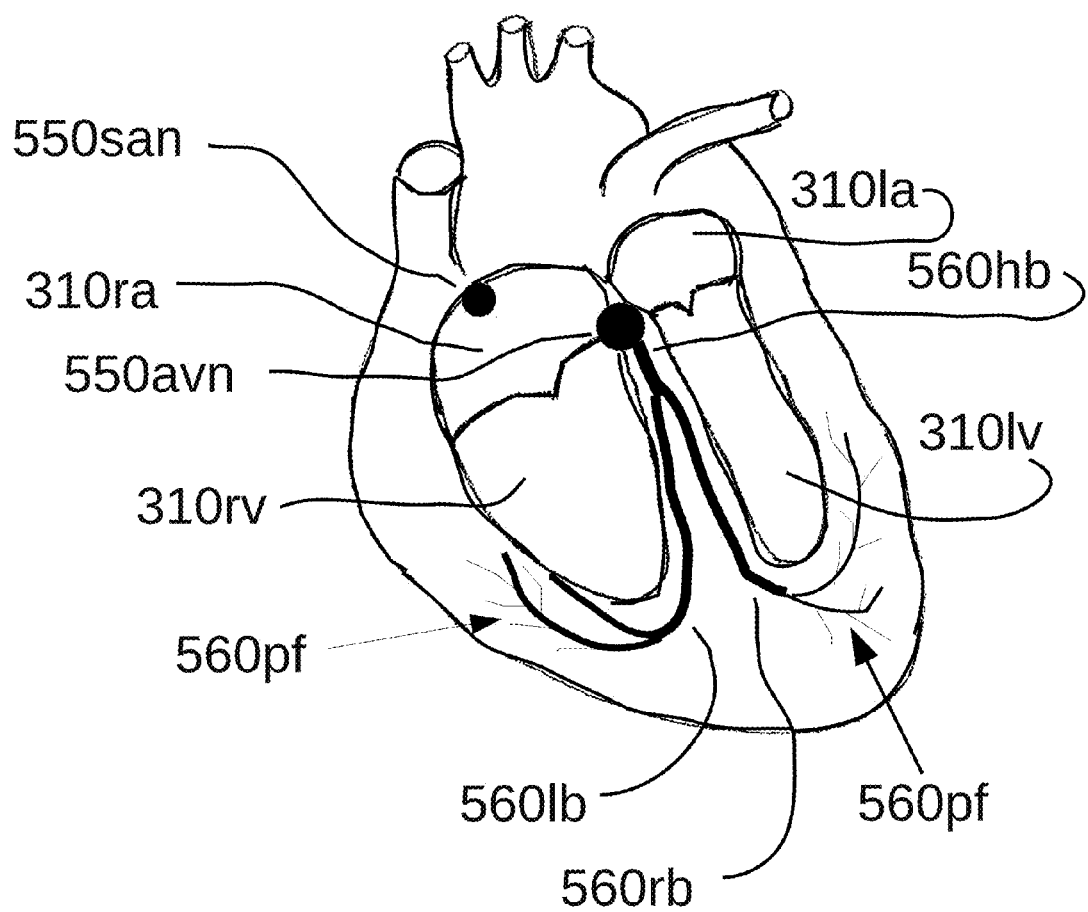
FIG. 5. Major parts of the normal human heart.

To understand the operation of our invention, the reader must keep in mind what causes the heart to contract, and therefore to pump the blood, and the sequential nature of this contraction as well. FIG. 5 displays a human heart with the main parts indicated in it. Left and right are designations from the point of view of the person in which the heart is, which is the opposite of the viewer, facing the person. The right and left sections are responsible for two independent closed cycle blood flow: the right side of the heart pumps blood to the lungs then back is the pulmonary circulation, while the left side of the heart pumps blood to the whole body. Note the four main chambers: right atrium (310*ra*), right ventricle (310*rv*), left atrium (310*la*), left ventricle (310*lv*), and some of the main parts of the heart: sinus node or sinus-atrial node (550*san*), atrial ventricular node (550*avn*), both of which are the starting points for the electrical pulses, the His bundle (560*hb*), the right and left bundles (560*rb*, 560*lb*) and the Purkinje fibers (560*pf*), which are the "fast wires" responsible for the fast propagation of the electric pulse from the atrial-ventricular node 550*avn* to the bottom of the ventricles, and the two inter chamber one-way valves: the tricuspid valve (on the right side) and the mitral valve (on the left side).

Figures 6A, 6B, 6C, 6D:
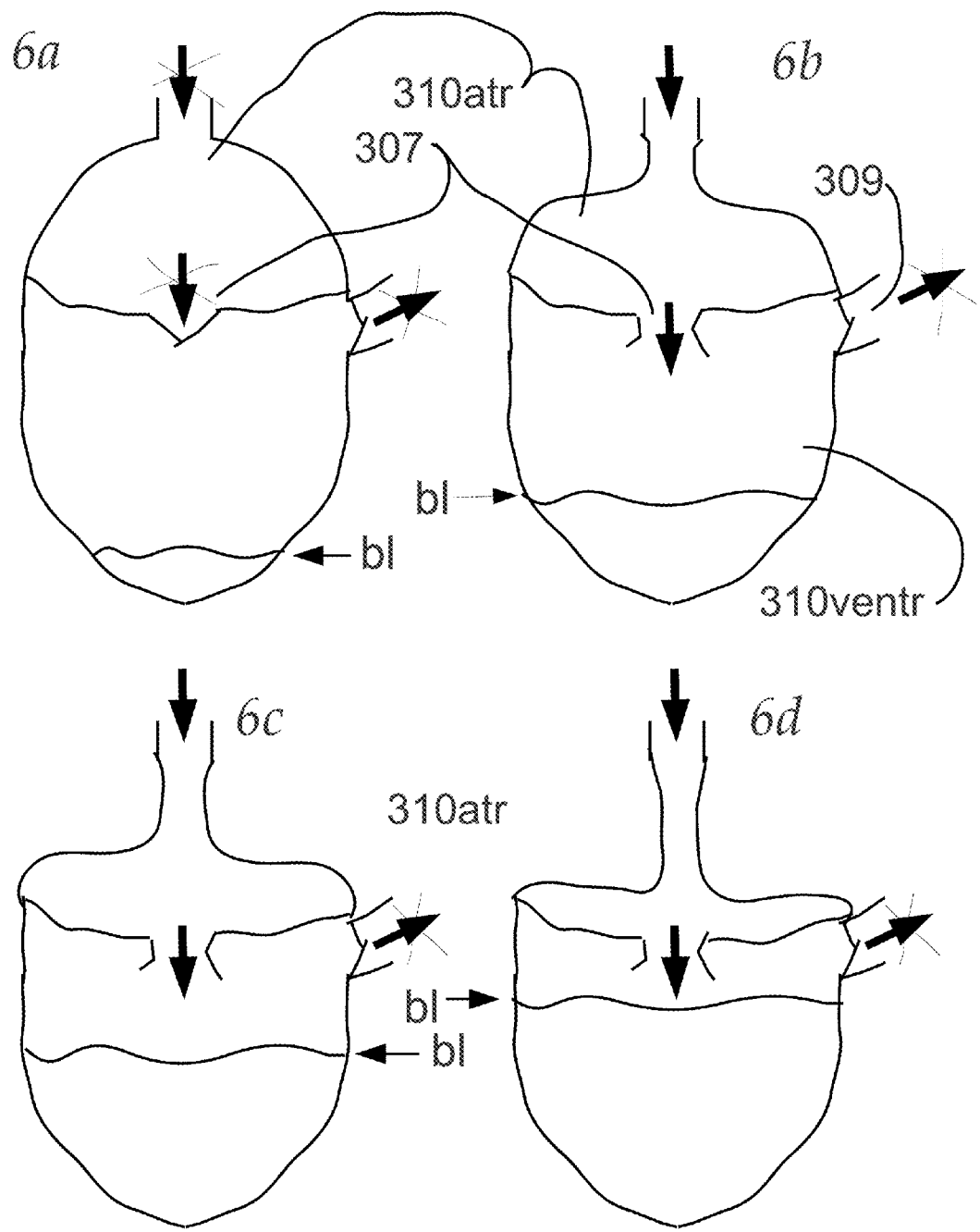
FIG. 6a, 6b, 6c and 6d. Four exaggerated sequential stages of squeezing the atrium (6a, 6b, 6c and 6d).
Figures 7A, 7B, 7C, 7D:
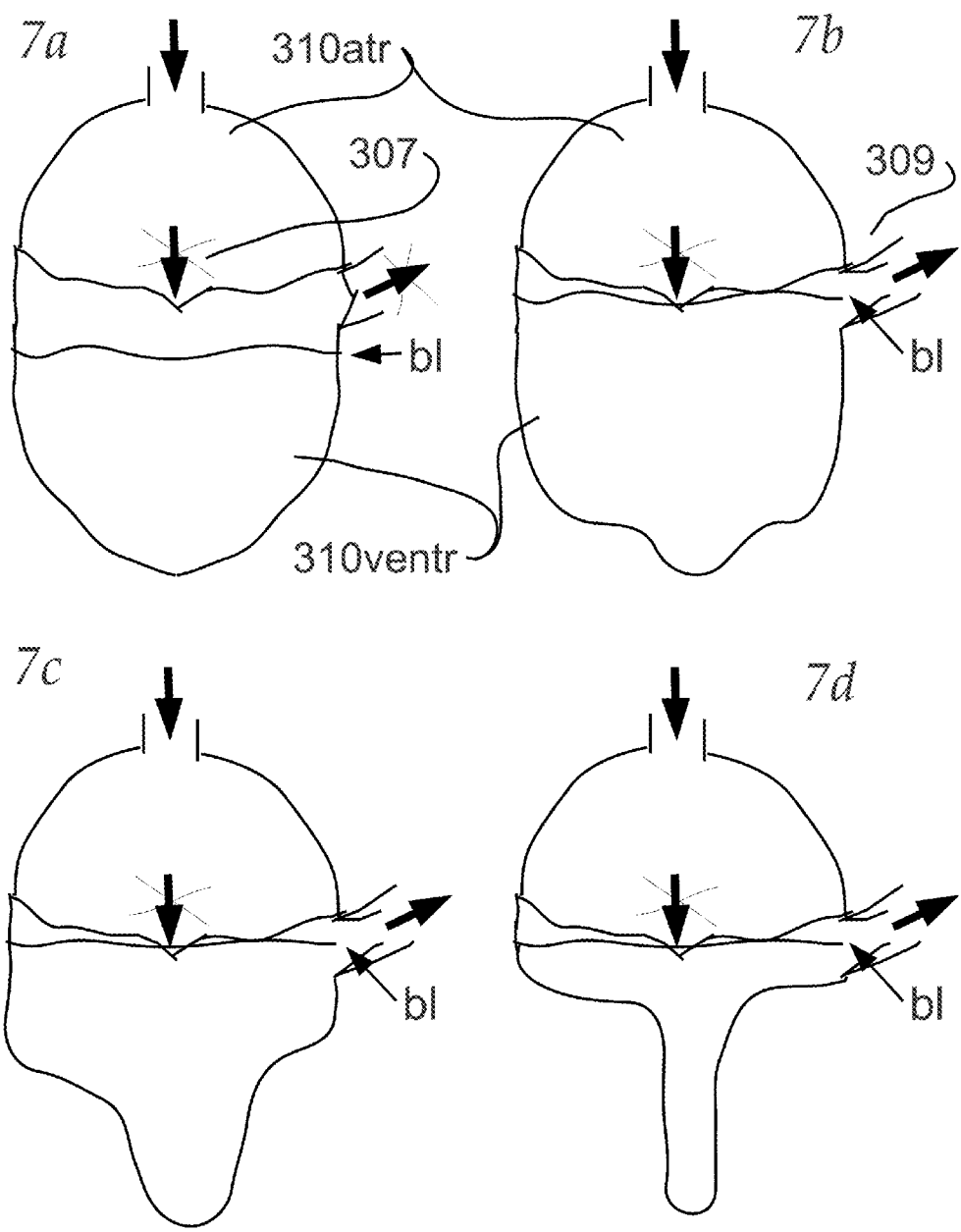
FIG. 7a, 7b, 7c and 7d are schematic representations of four sequential stages of squeezing the ventricle 310ventr (7a, 7b, 7c and 7d).

The heart muscle contraction occurs as a consequence of and following the propagating electric pulse that moves in 3-D (three dimensions) through the heart muscle from an initiating point (the sino-atrial node), which is located at the top of the right atrium—the 3-D electric pulse propagation through the heart muscle is important for the operation of our invention, as it will be seen in the sequel. This propagating electric pulse is known by the medical people as a depolarization wave, and the medical people associate a depolarization event to a muscle contraction event. This sequential contraction, as is the process of milking a caw, in which the milking person progressively squeezes from the top towards the bottom, forcing the milking down, as opposed to a simultaneous contraction from all sides, as is a collapsing air balloon collapsing upon itself from all directions at the same time, is less appreciated than it should, an often overlooked too, but it is nevertheless true that the heart muscle contraction is sequential, proceeding from the side further away to the exit port to the side near the exit port. One of the reasons for the lack of appreciation of this sequential contraction is that it is not perfect, as if it occurred within a well-engineered pump—the heart, and our body, for that matter, are actually poorly designed! This sequential contraction is valid for all four heart chambers: the right atrium, which has its entrance at the top and exit at the bottom, contains the initiating electrical cells at its top (the sino-atrial node), from which the electrical pulse propagates in its muscle walls from top to bottom, which is, accordingly, the sequential squeezing, as per FIG. 6*a*, 6*b*, 6*c* and 6*d*. Note that FIG. 6 is a schematic representation that exagerates the real heart contraction for illustration of the point. Blood is flowing from the upper atrium 310*atr* to the lower ventricle 310*ventr* through the opened one-way tricuspid valve 307. The exit from the ventricle 310*ventr* is through the pulmonary valve 309 at the top of the ventricle 310*ventr*, which is closed. The blood level (bl) at the ventricle 310*ventr* is indicated by the raising bl. The atrium 310*atr* keeps contracting from top to bottom, therefore squeezing the blood down through the one-way tricuspid valve 307. The ventricle, on the other hand, has both entrance and exit ports at its top, which poses a difficult problem to solve, needing as it does, to contract from bottom to top, to force the blood to exit at the top, while the electric pulse is coming from the top! This was solved by nature with a mechanism to arrest the electric pulse at the bottom of the atrium (else the ventricle would contract from top to bottom, where there is no exit point for the blood!), and another specialized set of cells, the atrium-ventricular node, which, upon receiving the weak electric signal that is coming down from the sino-atrial node, re-start another electric pulse, but with a few milliseconds delay, which is in turn delivered for propagation through a set of specialized fast propagating cells lining the wall between the two ventricles: the His bundle, the right and left bundles, and the Purkinje fibers. This second electric pulse, delayed from the initial pulse from the sino-atrial node, is then injected at the bottom of the ventricles, from where it propagates upwards, causing an upwards sequential contraction (in the opposite direction as the initial atrium contraction!), as required by an exit point at its top. This process of upwards contraction of the ventricle, the lower chamber, is displayed in FIG. 7*a*, 7*b*, 7*c* and 7*d*. It works, though any respectable engineer would have made a different design, with a ventricular exit at the bottom, not at the top, but at least one can take solace in that this is not the worse design error of the human body. FIG. 7*a*, 7*b*, 7*c* and 7*d* are schematic representations of the right part of a human heart, the left being essentially the same. Four sequential stages of squeezing the ventricle 310*ventr* (7*a*, 7*b*, 7*c* and 7*d*). During this second stage the one-way tricuspid valve 307 closes, preventing the blood from returning to the upper atrium 310*atr* as the lower ventricle 310*ventr* contracts from the bottom upwards. At the same time the exit one-way pulmonary valve 309 opens, allowing the blood to flow out of the ventricle 310*ventr*. The blood level bl is now fixed at the top of the ventricle 320*ventr*, which keeps contracting upwards from the bottom, forcing the blood out of it. The squeezing of the ventricle 310*ventr* is grossly exaggerated, as a normal heart squeezes only 55% to 70% of its blood volume out, and the squeezing is not as sequential as indicated in the figure, which exaggerates the situation for better observation.

The left heart pumping in essentially the same, varying only in minor details, there is no need to repeat.

This said, the reader should keep in mind two important points here which is the detail on which the whole invention hinges, and which we urge the reader to pay attention and ponder on. First, that not only is the heart contraction is caused by an electric pulse but also that this electrical pulse, because it relies on the propagation of heavy positive ions in a viscous medium, it propagates relatively slowly through its muscles and special fibers. The propagation of this electrical pulse is very slow as far as electric events happens, the whole process taking just below one second to complete (at a normal heart beating rate of 70 beats per minute). This means that the times involved are of the order of 10s and even 100s milliseconds. This slow propagation time is important for our invention to work, as it will become evident in the sequel.

In this main embodiment, the variation and improvement over our previous cited patents is that there are two types of electrodes (conductive and insulated, or active and passive), which are also of several shapes and sizes and randomly located on the surface of the device, while still attempting to cover most of the surface with electrodes. The random arrangement of the electrodes functions to break the space symmetry, therefore allowing better control of the injected current, which may need to be asymmetric—most likely will need to be asymmetric, following the heart shape, which is asymmetric. It is to be recalled here that no asymmetric electric field lines can be achieved using a symmetric electrode array, and further, that the resulting electric field shape necessarily have the same symmetry than the symmetry of the surface shape that produces it.

The shape and size differences is not necessary for the main embodiment, which would also work with electrodes (and non-conductive field shaping surfaces) of the same shape and/or size.

The invention is the same for simpler electrode arrays which may be simpler and less expensive to produce, such a choice being a matter of production/cost compromise, still under the scope of the main embodiment. For example, it is possible to control the vector injected electric current (magnitude and direction) with circular electrodes (of either type, conductive or current injecting and insulated or field shaping electrodes) that are of different sizes and randomly distributed on the surface of the piquita. It is also possible to control the vector injected electric current with circular electrodes (of either type), that are of the same size and randomly distributed on the surface of the piquita, in this more restrictive case, same shape and size but randomly distributed on the supporting surface. Or it is also possible to control the injected electric current vector with circular electrodes that are of the same shape and size and orderly distributed on the surface of the piquita, this being the most symmetric electrode arrangement of all. The difference between these options is simply the degree of possible variations and fine control on the vector current, and the choice between each option is based on a cost/benefit analysis, all being still within the scope of our invention.

A moment of thought will show the reader that the good operation of the heart depends on the propagation of the electric current. This latter depends on the electrical characteristics of the diverse muscles (cells) which comprise the heart, including rapidly electric propagating cells (His fibers, etc), endocardio and miocardio cells, all of which suffer individual variations from person to person, due to their genetic make-up, to which other variations accumulate during the person's lifetime, due to his exercise and eating habits, etc, to which unlucky events as small localized infarctions add scar tissues with lower conductivity and loss of contraction capability, all adding to a conceptually simple problem, yet of complex analytical solution. This, in turn, is the problem which our invention address: how to better adjust the 3-D electric current propagation through the heart in order to cause the best heart squeezing sequence possible for a particular individual, given his possibilities as determined by the physical conditions of his heart.

Another way to say the same thing is to notice that unlike a standard electrical network, on which the paths are discrete and fixed, the electrical path for the current that produces the muscle contraction is continuous over the whole 3-D structure of the heart, and some leak out of it too, being measured as EKG signals on the chest. Because the former, a standard electrical network is composed of discrete, enumerable paths, the information is given as the denumerable branches and nodes, while in the latter case (the heart) the information is a continuous current vector field.

Besides selecting which electrodes are turned on or off (connected or disconnected from the electrical power), another set of switches, also selected by their addresses, can select one of a plurality of voltages to be connected to the electrodes. Varying the voltage at the passive electrodes the device can adjust the electric field in its neighborhood, and therefore it can adjust the path of the electric current that is injected by the active electrodes. This offers an advantage over prior art because out invention can better direct the electric current to the particular desirable target volume and avoid entering into undesirable volumes.

The electric field lines.

Figure 8:
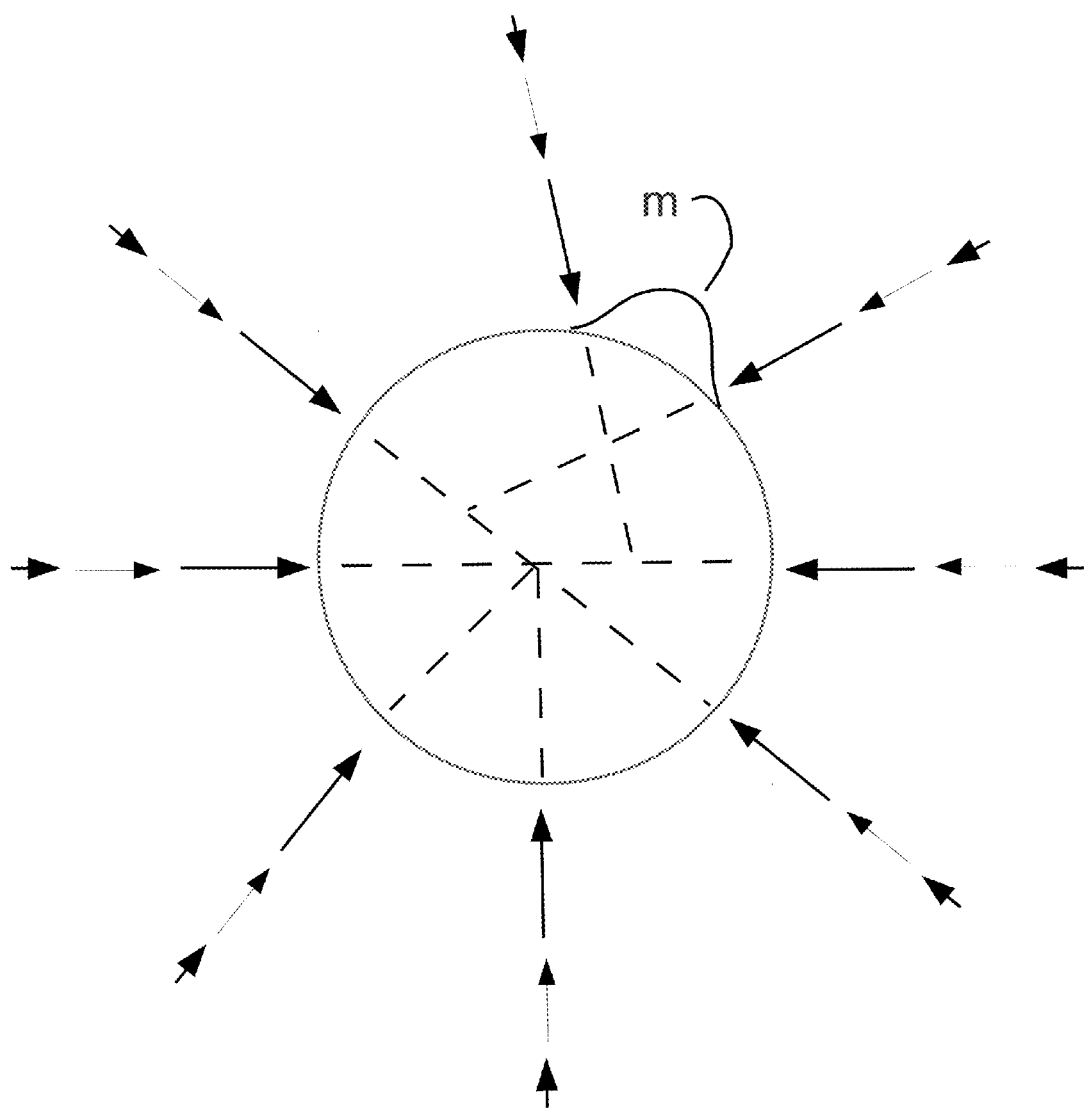
FIG. 8. The gravitational field of the planet Earth showing an exaggerated sideways deformation due to mountain m.

The solution to this problem is found in the theoretical analysis of electric current propagation within an electric field. As a side remark, this is similar to the motion of an object by gravity within the gravitational field of the planet, which is vertical towards the center of the planet assuming a perfectly spherically symmetrical Earth. All objects, unless prevented from falling by some means, do fall down in the direction of the center of the Earth, on a straight vertical line. The earth gravitational field is set of lines radially pointing to its center, as most of the fields in FIG. 8. FIG. 8 also display two gravitational field lines next to an exaggerated large mountain, which, due to its large mass tilts the gravitational field lines sideways towards the mountain. An actual large mountain does, surprisingly enough, minutely deflects the gravitational field from its "normal" direction towards the center of the earth, and in amounts that are detectable with modern equipment (see an exaggerated off-radial displacement near the mountain at FIG. 8). This, of course, happens because the mountain attracts sideways.

Given that $$F(vector)=q \times E(vector),$$

Figure 9A:
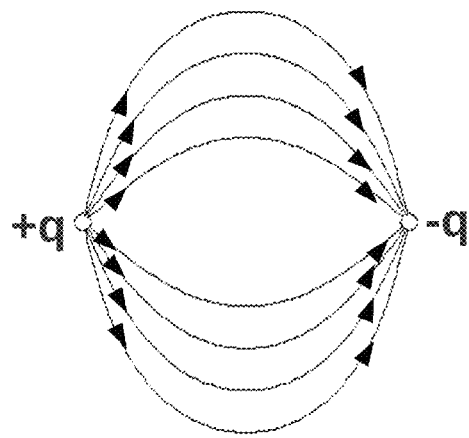
FIG. 9(a, b and c) Show three examples of electric field lines (which are the lines along which a positive charge would move).
Figure 9B:
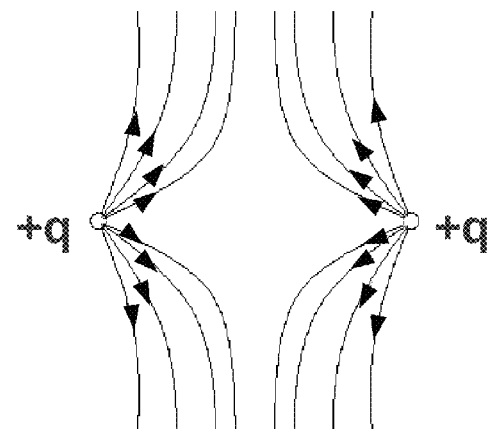
Figure 9C:
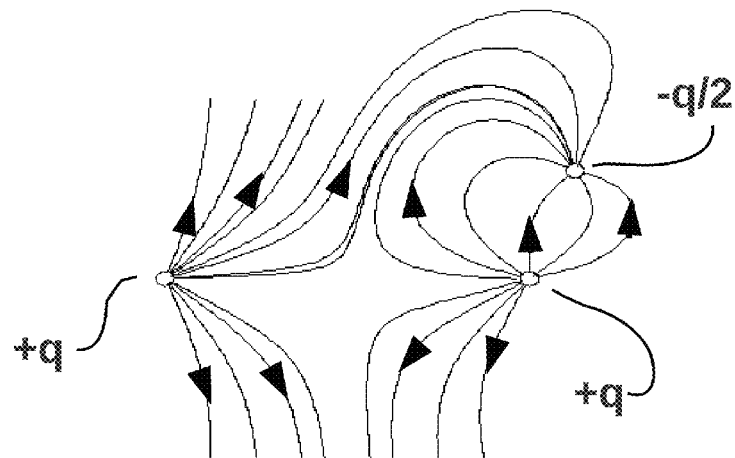

It follows that the force, and consequently the acceleration and then the motion of an electrically charged particle starting from rest follows the electric field lines. The electric field can take more complex configurations than the gravitational field, because there are two types of electric charges (usually called positive and negative), while the gravitational field is due to only one type of gravitational charge (called mass, they all attract each other). FIG. 9 (a, b, c, d and e) displays five types of simple electric field configurations: FIGS. 9a and FIG. 9b display two cases of field lines that are simpler to calculate, of two electric charges, in fact the configuration normally seen in introductory physics books. The field lines are the lines along which an electric charge moves if left unconstrained to move. In other words, the field lines control the flow path of the injected current. From this it follows that to shape the electric field lines is the same as to lay down the "roads" where the current will travel whenever charges are set free in the region. This notion of shaping the field lines to determine the current path is seldom used only because in most electric circuits the current (charge) is forced to follow the wires, the coils, the transistors, etc., with no place for an externally imposed electric field to have any effect. FIG. 9c shows a more complicated case with three charges: +q, +q and −q/2. The reader should notice that such slightly differences in charges produce vastly different shapes of the electric fields, which are the paths of charges free to move in the space in each configuration.

Figure 9D:
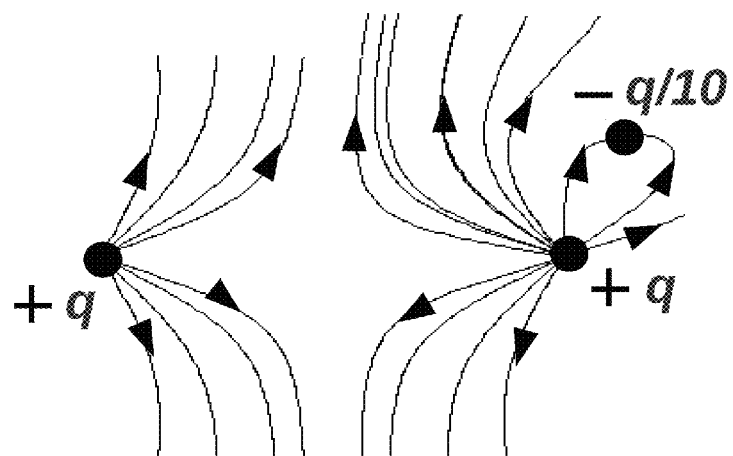
Figure 9E:
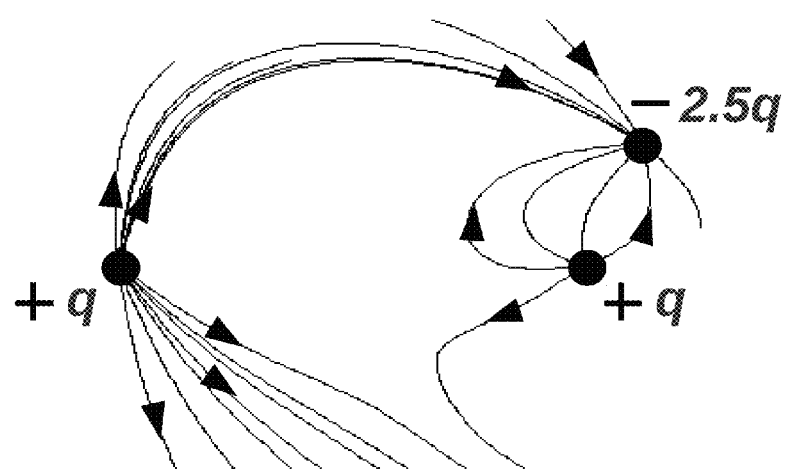

The space may be around a heart, for example, so each case causes a different heart contraction sequence. The reader is invited to observe the large change of the configuration of the field lines caused by the addition of this third charge, in particular the disappearance of the symmetry that is obvious in FIGS. 9a and b. FIGS. 9d and e display the effect of varying the value of the third charge. Again the reader is invited to ponder on the consequences of varying the values of the charges. The reader will notice how vastly different the field lines are with a simple change of one charge from a small value of q/10 to a larger value of 2.5 q. Notice that both FIG. 9d and FIG. 9e are asymmetric, yet the shape of the field lines is vastly different between them!

The electric field lines are distinctively unequal, very different shapes. Not displayed is also their strengths, which is also distinct, left out to simplify the FIG. 9 illustrates the point of our invention: a method and a means to conform the electric field lines to the desired 3-D shape required for a most desirable heart squeezing sequence. In fact, using the piquita of our invention, it is possible to even create a 3-D electric field which causes a better heart squeezing sequence than the sequence that happens in a normal, healthy heart, because a normal, typical, healthy heart does not actually follow the best possible sequence.

Setting each small electrode at the surface of the piquita at a different electric potential (which causes a different electric charge Q on each electrode), a different electric field is set in its neighborhood. The cardiologist, or any other medical personnel, using a computer program to display the electric field created by any particular combination of voltages, will adjust the voltages at different electrodes and see, on the computer screen, the 3-D conformation of the electric field created by them. This is one problem of the class known as "inverse problems", a technical name given in mathematics for problems in which a particular cause is sought (a particular distribution of voltages on the surface of the piquita) which will cause a particular 3-D electric field configuration over the heart muscles. Most inverse problems have no closed form solution, not does this one. Its solution is found by trial and error, adjusting a new voltage distribution and noticing if the new electric field got closer to the desired one or farther away from it. From this, readjust the voltages and observe the result again, and again, etc. Though this may seem a tedious solution, it is easier than working from scratch, because the hearts are approximately the same, and the pacemakers are implanted in approximately the same places, which means that the general type of solution needs to be found once and for all—then only smaller adjustments are necessary. In any case, if so desired the cardiologist can set all the active surface to be at the same electric potential (voltage), in which case the "improved" electric stimulator (pacemaker) would be working in the same way as prior art pacemakers. In practice, the inventors believe that even without individual adjustments, and only using the best average selection of surface distribution of electric potentials (voltages), there would be some improvement over prior art.

Current art of heart pacemaking uses two and even three individual electrodes, for example, one electrode near the sino-atrial node (at the top of the right atrium), and one near the bottom of each ventricle (right and left). Multielectrode stimulators much enhance the performance of our invention, because they increase the number of available points over which there is control for adjusting the voltage V (or charge Q, which is the same thing), and also at much larger distances between them. More control is possible with the modern two- and three-stimulators than with the one single electrode at the top of the atrium.

Figure 10:
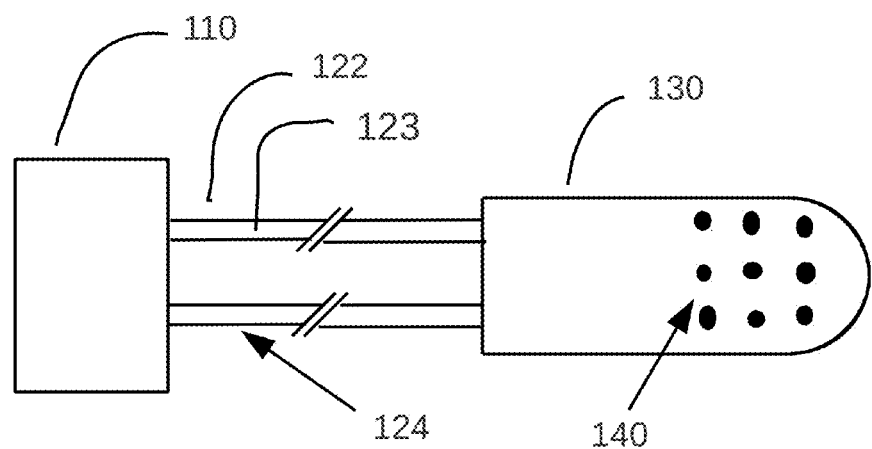
FIG. 10 A picafina brain-style stimulator with equal circular electrodes.

Another feature of our invention is the use of the passive (type-2) electrodes. These are electrodes covered with an insulating layer, so they cannot inject electric charges on their surroundings, and can be used only to shape the electric field. This adds flexibility to the device, because the electric field shaping should be made without changing the injected current. In fact, prior-art also shaped the electric field (any charge or voltage distribution does create some electric field around it), only that it was not a shaping done on purpose to achieve the best contracting sequence. In fact, prior art consistently created a symmetric field, possibly an almost spherically symmetric electric field around the electrode. The passive (type-2) electrodes disclosed by our invention allows for flexibility in the capability of shaping the electric field in the heart independently of the electric charges injected. Electrodes of both types are randomly spread over the surface of the supporting piquita structure so as to allow injection of charges from every point that is desired and the maximum use of surfaces to shape the electric field independently from the electric current injection. The shapes of the electrodes may be random, as in FIG. 1, or fixed, as in FIG. 10, which is for another embodiment, for brain electric stimulation, which uses circular electrodes. Our invention does not need to use randomly shaped electrodes as shown in FIG. 1.

The electrode addressing is made in any of the standard ways, for example, a comparator that matches an incoming address with a hardware written address for each electrode (FIG. 3). When address matches a switch is closed connecting the electrode to one of a plurality of voltage sources. The addresses are preferentially sent via serial bus, as a USB bus, which is decoded at the device as described in US applied patent (Chong_Monteiro_2011_SerialAddressing)

Besides the directional electric current flow, which is started again at every heart beat at the sinoatrial node, the local reactance plays a role, as it determines a 3-D continuous network which determines the time delay and magnitude of the local electric pulse, which in turn determines the local timing and strength of the local squeezing. Incorrect time delays of the electric pulse are costly for the pumping efficiency, because they are the very cause of the muscle contraction, that is, of the pumping, and localized higher or lower resistivity are costly too, because they change the electric current intensity, which in turn decrease or increase the strength of the muscle contraction, that is, of the pumping pressure, either way decreasing the total pumping volume. Our invention, as it adjusts the magnitude and the direction of the electric field throughout the heart muscle, corrects for these errors that accumulate throughout the life of the person, as the heart ages and changes.

Taken together, controlling the direction and the magnitude of the current, our invention is capable of controlling the position and the magnitude of the squeezing sequence.

Introduction to the mathematical treatment of the problem of the best electric current distribution over the heart muscle.

It is a well known result in electromagnetic theory Reitz, Milford and Christy (1980), Jackson, (1975) that any arbitrary vector field inside a closed (imaginary) surface obeying the ordinary laws of fields that govern the electric charges, can be created adjusting the values of the vectors at the surface that encloses the closed volume. This latter is achieved by appropriate charges on the imaginary surface. This physical statement is related to the Dirichlet's principle DIRICHLET (n/d) In our case the stimulating device does NOT have total control, because it would be impossible to set voltages at unconstrained values (the electric energy source/battery is rather limited on its maximum output), nor do we have access and control over some surface that completely encloses the heart (or the brain, etc.), which means that not all desired vector fields are possible. Yet, adjusting the available electric potentials (voltages) over the available surface on the device in the vicinity of the desired volume it is possible to have a certain degree of control of the current vector field over the heart volume. This is even more correct when the piquita stimulator is, as is becoming more common nowadays, a three independent stimulators, one at the top right atrium, one at the bottom of each ventricle. Our invention does not create a total control on the field lines, our invention cannot create all arbitrary field shapes, but our invention can shape the field to a better conformation than old art which offered no control of it. In fact, to the best of the knowledge of the inventors, nobody before have ever tried to control the electric field shape on the heart muscle to control the current through it.

Dirichlet's problem is discussed in books dealing with electromagnetism because it is much related to the problems of interest in the field, yet it was initially developed out of its mathematical interest, and it is also discussed in many books in differential equations.

This mathematical theory indicates that our invention works better with either a larger area supporting electrodes (which approaches a totally containing surface) and also with just a few small electrodes spread apart, as in the two- and three-electrodes of current heart pacemaking, anchored as they are, at the top of the right atrium and bottom of each ventricle.

Therefore our invention is the use of a controlled charge distribution (or voltage, which is the same, because one determines the other) over as large an area as feasible, with the objective of adjusting the electric field lines over the heart muscle so that the injected current causes a downwards moving current from the top of the atrium to the boundary between the atrium and the ventricle, then either another current through the His bundle, right and left bundles and Purkinje fibers, or else simply another starting electric current originating on another implant at the bottom of the ventricle, possible if the cardiologist decides to use a two-electrodes pacemaking system. Moreover, the surface electrodes can be of either type 1 (active) or type 2 (passive). The first type of electrode can be either starting or finishing points for electric current paths, while the second type of electrodes is able to bend the field lines but not able to inject charges, because it is electrically insulated (though it can act via capacitive effect, as well known to the persons versed in the field of electrical engineering). Finally, given that the times involved are very long for electronics, a typical heart period being almost a full second and its P, Q, R, S and T waves lasting from a few to 10s milliseconds, while microsecond is easy in electronics, it is perfectly feasible to activate electrodes or either type (active or passive types) then turn them off sometime before the slowly moving electric current arrives at the electrode, therefore forestalling the establishing of a terminal point for a current. This can be dynamically adjusted to keep the current moving along a desired path, while never absorbing it. This selective adjusting of the ending points of an electric field line is effective in creating strong field lines with the use of electric charges near the initiation point of the current, which in turn is made to disappear as the current nears intermediate positioned electric charges, which may be substituted by other charges further along the desired path, all working as a carrot moving ahead of a running rabbit. Of course that the reverse action can be also created, of a same sign charge being introduced behind the moving current, in which case this same charge could be seen as akin to a whip at the back of the moving current, a horse-type incentive added to a rabbit-type one.

Two and three electrodes heart pacemakers are becoming common nowadays, and more electrodes may be used if a good reason for them is discovered, as our invention does. Even three anchored heart piquitas in three different places already open new possibilities for shaping the electric field; more than three offer even more possibilities.

DESCRIPTION AND OPERATION OF ALTERNATIVE EMBODIMENTS

Figure 11:
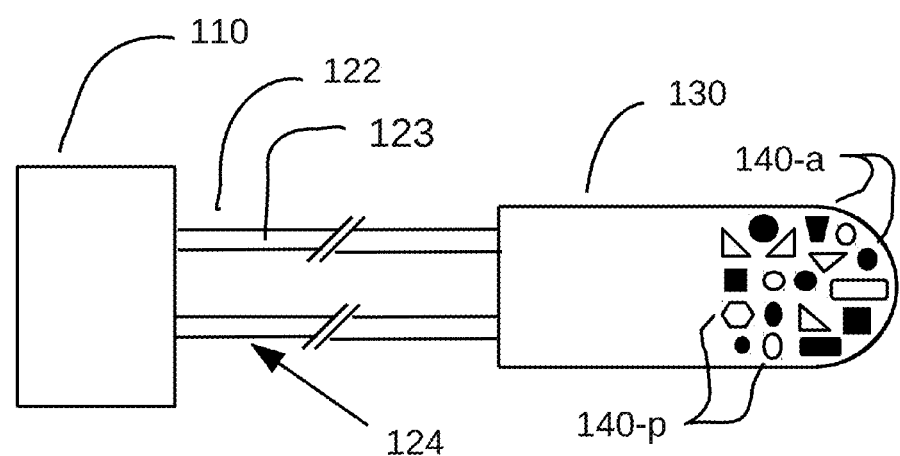
FIG. 11 Shows a version of our invention for Deep Brain Stimulation.

Another embodiment of our invention is application to DBS (Deep Brain Stimulation). In this application the objective is to disrupt the anomalous neurons firings that cause the tremor characteristic of Parkinson's disease, or of what is known as essential tremor. One of the possible solutions is to place an electrode on a chosen target area in the brain then superimpose a current of frequency around 200 Hz on it. FIG. 11 shows a brain-type stimulator (picafina), similar in structure to prior art stimulators with 4 rings at their distal extremity (Medtronic (n/d) and Butson and McIntyre (2006)) but with the equivalent electrode structure shown in FIG. 1 for a piquita, which is similar in structure to the piquita stimulator of our invention, or heart-type stimulator (heart pacemaker). The objective for the Deep Brain Stimulator (DBS) is to adjust the electric field in the vicinity of the brain electric stimulator, which we call picafina or picafina-style stimulator, to the shape of the particular target volume, which could be the sub-thalamic nucleus (STN), the globus pallidus interna (GPi) or any other. Much effort has been put on the solution of this problem, the solution of which has evaded the practitioners of the art for decades—see, for example, Butson and McIntyre (2006). It can be seen at Butson and McIntyre that the best solution proposed is still a symmetric field. Such a symmetric field fail to offer a maximum electrical stimulation in any case, particularly when the electric stimulator happens to have been implanted off-center. As discussed by Butson and McIntyre (2006), this is, in fact, a most common occurrence, due to the small size of the target volumes and their location deep in the base of the brain (for DBS), which is also not directly observed by the surgeon, which inserts the electric stimulator through a one-cm diameter hole drilled at the top of the skull, from where he/she tries to guide the stimulator tip to the desired target. Our invention allows for more control of the electric field around the stimulator, which in turn, allows for better clinical results.

Figure 12:
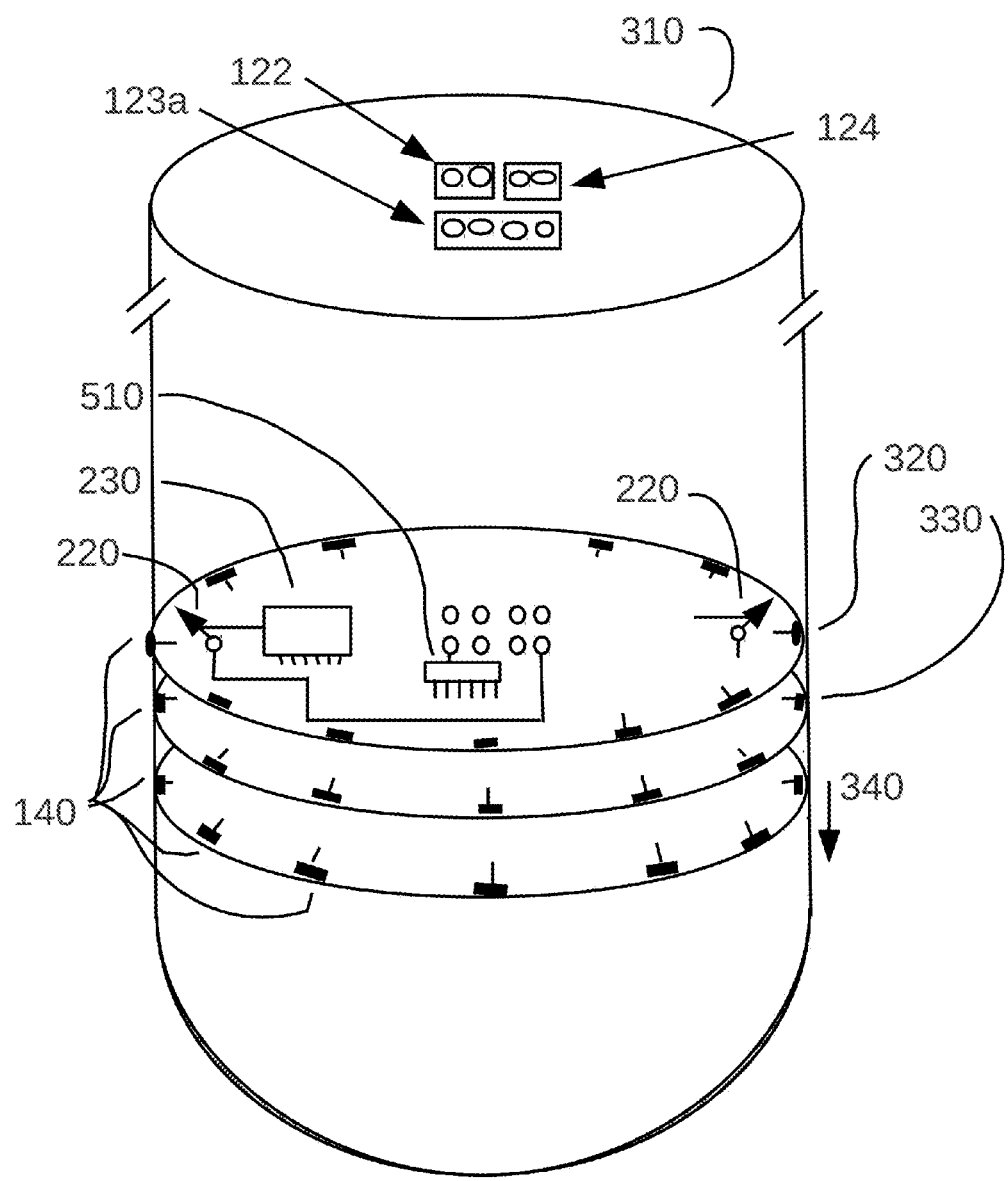
FIG. 12 Shows a perspective view of a picafina brain-type stimulator of our invention.

FIG. 12 is a perspective view of a picafina brain-style stimulator. In it, 122 is the serial data and return, 124 is power and return lines, and 123a is a plurality of control, 320 is the topmost layer of electrodes 140, 330 is the next lower layer of electrodes 140, 340 representing a series of a plurality of layers of electrodes 140.

Figure 13:
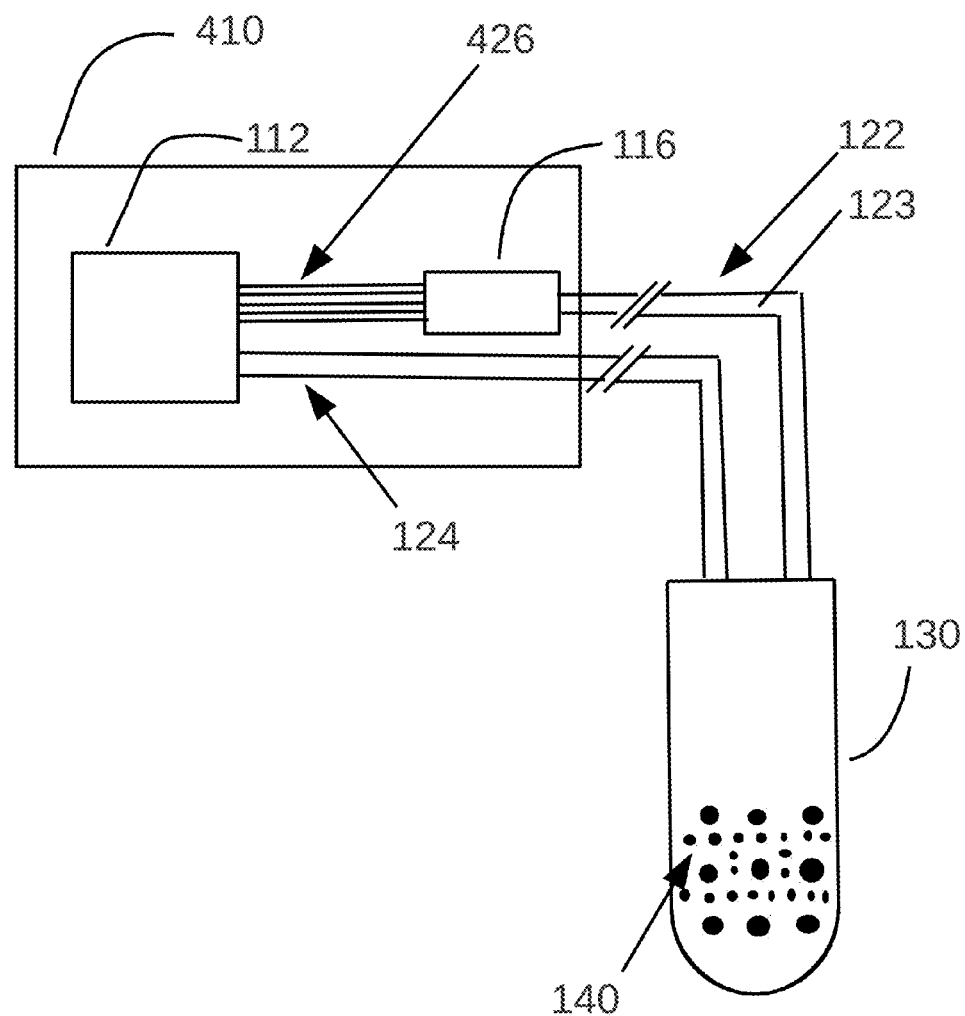
FIG. 13 Shows a schematic connection between the sealed box and a brain-type picafina stimulator of our invention.

FIG. 13 shows another schematic view of the picafina brain-style stimulator, though the schematic representation could transfer to the heart-type piquita, to the planar type, and any other. In it, 410 is a hermetically sealed box, which in prior art is normally made of titanium or any other bio-compatible material, the energy storage unit 110 (battery) and the microprocessor MP1 are omitted for simplicity, 112 may be part of the microprocessor MP1, 116 is a serial-to-parallel converter, 426 are the parallel address lines coming from some part of microprocessor MP1, 124 is the power, transferred from the energy storage unit (battery), 122 is the serial address line, 123 is the control data line, 130 the picafina stimulator-type, and 140 the plurality of electrodes, which in this figure are not differentiated between active and passive, for simplicity.

FIG. 14 shows another schematic diagram of a picafina brain-style stimulator of our invention. In this figure due to space limitations and for simplification, there is no differentiation between the two types of electrodes: type1 and type2. The same principles are applied to the piquita heart-type stimulator and to other variations of it.

The electrodes for DBS can be of different size, of different shapes and also randomly distributed on the surface of the supporting structure or picafina, or they can be of uniform size and shape, perhaps to decrease manufacturing cost, for example, or to simplify the internal electronics, or any other reason. Given the small size of the electrodes, random shape of them is of smaller effect than their numbers, while the use of the two types of electrodes, active or type-1 electrodes and passive or type-2 electrodes are of major importance, given that the latter only change the electric field shape around the stimulator device.

The reader will notice that the DBS application is a natural adaptation of all that is described for the heart pacemaker. A multiplicity of electrodes, of variable shapes and sizes, each associated with a unique address (a numerical address, or a numerical "name" if you will), which is used to select which electrode is turned on, which electrode is turned off, both for type-1 (active) and type-2 (passive). Likewise for the heart pacemaker, the DBS incarnation uses two types of electrodes: a first type, or active type, capable of injecting a current, and a second type, or passive type, which is insulated, not capable of injecting any current (though always there is a small leak current due to imperfections), but which is much useful for creating the vector field around the electrode, which, in turn, determine the 3-D path for the injected current.

Another possible application for the invention is for appetite control. In this application there are two possibilities: electrical stimulation on the stomach, and brain stimulation at the locations which are known to control the appetite. In the former case the added electrical stimulation may be turned on before a meal, and the electrodes are selected to affect the neurons that send information to the brain regarding the current amount of food in the stomach, which in turn modulate the appetite. If the stimulation is capable to fool the brain, the individual will feel a decreased urge for food, eat less, and lose weight on the long run. This has been used in humans already. The second case, brain stimulation to control the appetite has been only used in animals so far, and with success. For stomach stimulation the shape of the stimulator should be a flat shape to conform to the curvature of the stomach and its enervations. For direct brain control it may be similar to the DBS.

Another possible application is for cortical brain stimulation, in which case the stimulator has a flat shape to adjust to the cortical application.

Another possible application is for pain control, an improvement of a known device known as TENS (Transcutaneous Electrical Neural Stimulation). In this application the objective is to control superficial pain, as skin pain, and it has used for deeper pain too, as muscle pain. The area (here it is really area, the surface area of the skin in question, not what the neurologists call area, which is a volume) in question is in this case surrounded by electrodes attached to the skin, from which there is a current flow. Old art used large electrodes, which did not allow for a control of the current path. In this case our invention discloses a large number of small electrodes which are on the surface of the applied patch. Likewise the heart pacemaker, these small electrodes are numbered (their address), are of two types (type-1, or active, and type-2, or passive), and can likewise be turned on or off. With a wise selection of the active electrodes, it is possible for the medical practitioner to ameliorate the pain felt by the patient in a more effective way than currently used TENS devices.

The individual electrodes, which in the main embodiment are randomly spread on the supporting structure (picafina), and are of various shapes and sizes, can be all of the same shape and/or same size, and/or can be arranged on an orderly arrangement too. In such a case the advantage of maximal symmetry breaking is not achieved, but some partial symmetry breaking is still obtained with the selection of particular electrodes as the points from which to initiate the stimulation, and the selection of other particular (insulated) electrodes from which to originate the field shaping lines. Cost and other factors could determine a simpler regular electrode arrangement. More orderly arrangements of the electrodes than the arrangement disclosed in the main embodiment, which provides maximal advantage, are still in the scope of the invention.

Persons acquainted with the art of symmetry will recognize that for very small electrodes with small spacing between each, there is little gain if compared with larger electrodes of variable shape and sizes, as particular sets of smaller electrodes can approximately create the shape of a larger electrode of any arbitrary shape. Cost and programming time may dictate one type of another of electrode, and their size and placement, while these variations are still covered in the scope of the invention.

The relative distribution of the electrodes of type-1 and type-2 (current injecting electrodes and electric field shaping electrodes, or magnitude and direction determining electrodes) is random in the main embodiment of this invention, but it is possible to alternate electrodes from type-1 to type-2, then type-1 again, etc., when the electrodes are of the same size and orderly distributed on the surface of the stimulating piquita, picafina and their variations devices.

Figure 15A:
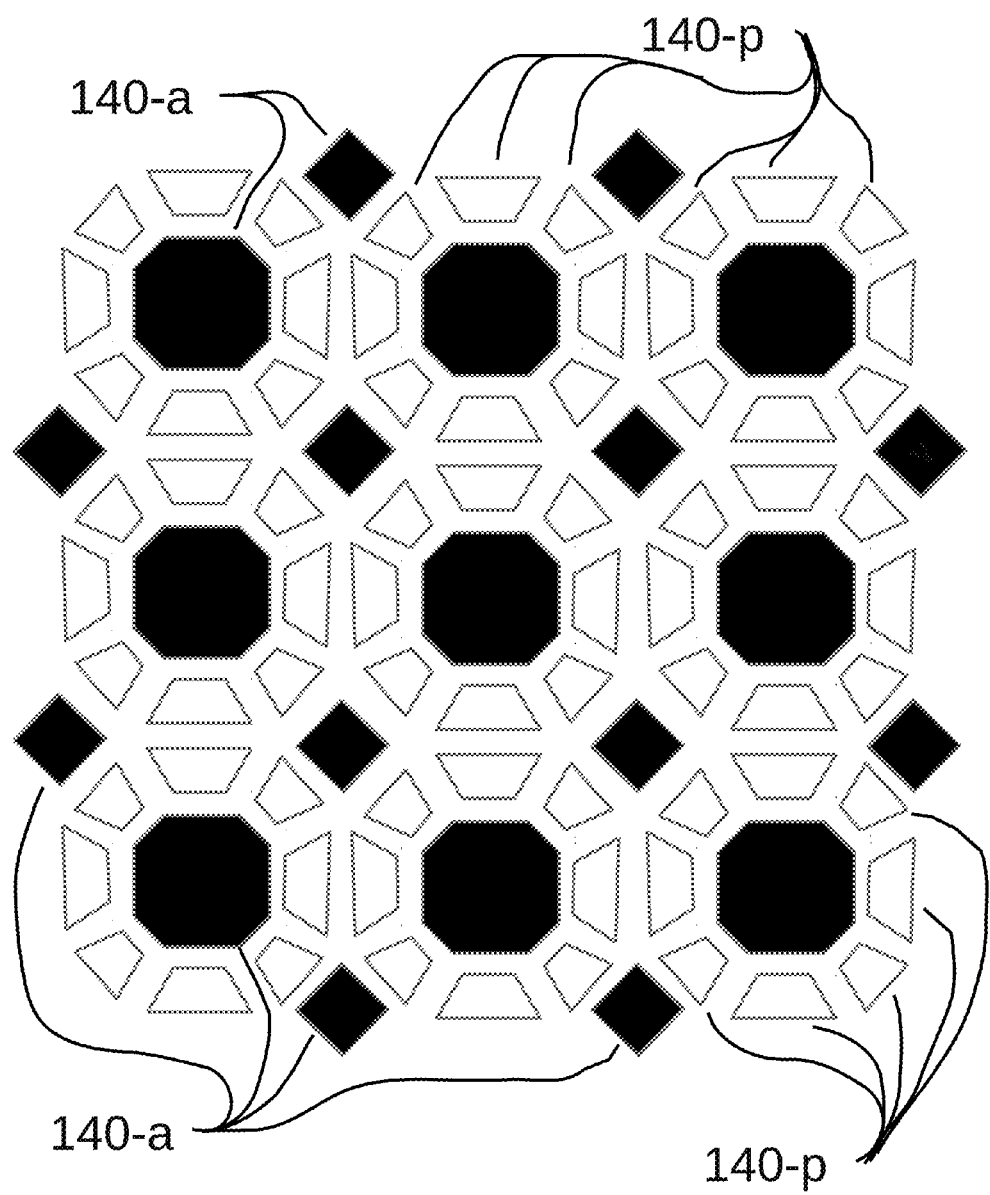
FIGS. 15a and 15b Shows two variations of electrode shapes.
Figure 15B:
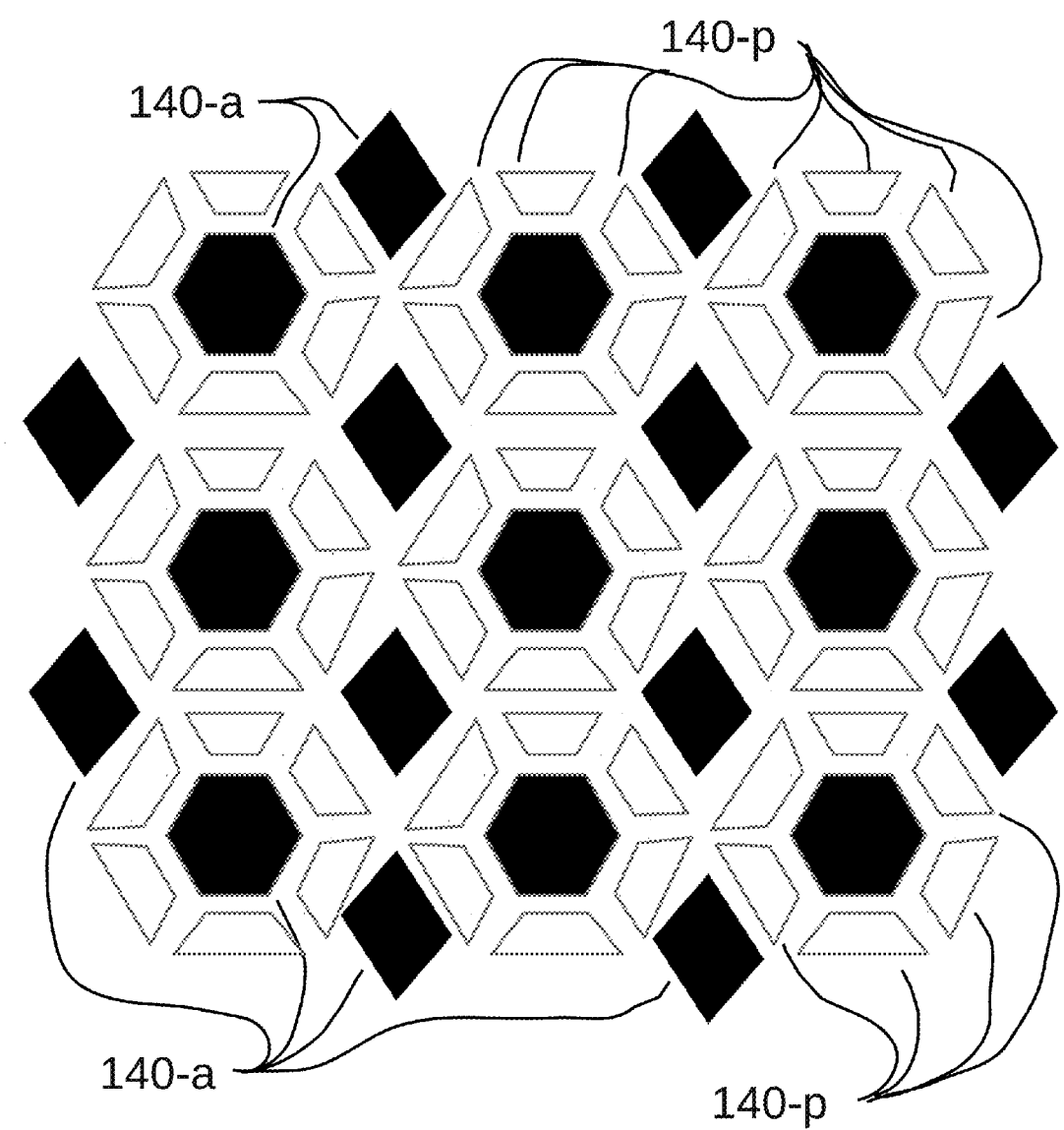

One important pattern for the electrodes is the hexagonal pattern, which is shown in FIG. 15b, and other variations of it, as the octagonal pattern, shown in FIG. 15a. FIGS. 15a and 15b show two possibilities of the many, with the surrounding electrodes of the active type and the center (hexagonally shaped, octagonal shaped, etc), and the electrode of the passive type surrounding as needed. Other combinations are possible. It is, of course, possible to use only hexagons, because they completely fill a 2-D space. In this case type-1 and type-2 electrodes would alternate, or they could also be random. This particular electrode distribution is symmetrical, which is a departure from the main embodiment, but, given that the electrodes are small, most asymmetric shapes can be approximated. Variations of FIG. 15 are reversing black with white electrodes (that is, reversing active and passive-type), or making them random, each electrode, regardless of their position, center hexagon or one of the surrounding six parallelepid, being assigned randomly to be active or passive. In later use, it is a computer program that determines, from mathematical calculations, which of the electrodes are on and off, in order to create the desired field shape.

Persons familiar with the art understand that the hexagonal pattern displayed at FIG. 15b is just one of the many possibilities. Triangular arrays square arrays, rectangular arrays, and others are possible, these being examples of arrays that completely fill the space. But the individual units do not have to even completely fill the available space, because maximal asymmetry (maximal lack of symmetry, or maximal symmetry breaking) is achieved with random distribution of electrodes.

CONCLUSION, RAMIFICATIONS, AND SCOPE OF INVENTION

Another way to see the control of the paths of the current in the heart, or the extent of electrical stimulation in brain DBS, etc., is to look at the active electrodes determining the magnitude (and also the direction in a limited way too) and the passive electrodes determining the direction only of the current. In this view one considers the stimulating current as a vector which follows the electric field lines.

Other options are possible for the marker 140-m that indicates the angular position of the piquita as implanted. For example, all the electrodes may have enough X-ray opacity to show in the fluoroscopic images taken during the heart pacemaker implantation. Or one or more or the anchoring arms 131 may be smaller (or larger), or each anchoring arm may be of a different length and/or diameter, to allow their identification.

The addressing system used to select which electrodes are used may, in certain situations in which space for wiring is not at a premium, be send in parallel, instead of serial fashion, as in the main embodiment, without changing the fundamental aspects of the invention, still within the scope of the invention which is the use of several electrodes of varying shapes and sizes, randomly positioned, and of two types: one to determine the magnitude of the injected current (controlling either the voltage or the current, first electrode type), and another to determine the direction of the injected current (controlling the electric field lines through the process known as field shaping, second electrode type). One such case is a TENS device (Transcutaneous Electrical Neural Stimulation), which is totally outside the patient, with plenty of space for a large number of wires. In this case of TENS it would be advantageous to use more wires, parallel transfer of control, data and address, avoiding the extra cost of the parallel-to-serial conversion then later the serial-to-parallel conversion.

The main embodiment for heart stimulation uses a simple version of stimulation, which is fixed and continuous, of the type of the old heart pacemakers. It is possible to have stimulation on demand too, as many current pacemakers have, which is based, for example, on activating the stimulation only when the natural pacemaker becomes insufficient, or stops, or becomes erratic. This is called stimulation on demand, easily incorporated in our invention that already contains a microprocessor capable of implementing such decisions. Such extensions are part of the current art of heart pacemakers and may or may not be incorporated in our invention. Our invention is independent of stimulation on demand.

One skilled in the relevant art, however, will readily recognize that the invention can be practiced without one or more of the specific details, or with other methods, etc. In other instances, well known structures or operations are not shown in detail to avoid obscuring the features of the invention. For example, the details of the address decoder, or the details of the serial-to-parallel conversion are not shown; these are well known in the art of electronics and can be realized in several different ways, many or most of which are compatible with the invention, and therefore the details of these, and other details are not included in this patent disclosure.

SEQUENCE LISTING

Not applicable

REFERENCES

JamilleHetke_Kipke_Pellinen_Anderson_ModularMultichannelMicroelectodeArrayEtc_USPTO-PatPubl-US2007-0123765_070531

Butson and McIntyre (2006). Christopher R. Butson and Cameron C. McIntyre "Role of electrode design on the volume of tissue activated during deep brain stimulation" Journal of Neural Engineering, vol. 3, pgs. 1-8 (2006)

Chong Il Lee and Sergio Lara Pereira Monteiro (2011) "Method and means to address and make use of multiple electrodes for measurements and electrical stimulation in neurons and other cells including brain and heart" U.S. patent application Ser. No. 13/053,137, Mar. 21, 2011, not yet published.

Chong Il Lee (2010) "Method and means for connecting a large number of electrodes to a measuring device" US patent application number 20100079156, published Apr. 1, 2010

Chong Il Lee and Sergio Lara Pereira Monteiro (2010) "Method and means for connecting and controlling a large number of contacts for electrical cell stimulation in living organisms" U.S. patent application number 20100082076, published Apr. $1^{st}$, 2010.

DIRICHLET—http://en.wikipedia.org/wiki/Dirichlet_principle

Jackson (1975) Jackson "Classical Electrodynamics" Wiley.

Thaler (2003) Malcolm S. Thaler "The Only EKG Book You'll Ever Need", Lippincott Williams & Wildins, $4^{th}$ ed. (2003).

Medtronic (n/d) Medtronic website with info on DBS leads.
http://professional.medtronic.com/pt/neuro/dbs-md/prod/dbs-lead-model-3387/index.htm
http://professional.medtronic.com/pt/neuro/dbs-pd/prod/dbs-lead-model-3391/index.htm Reits, Milford & Christy (1980), John Reitz, Frederick Milford, Robert Christy "Foundations of Electromagnetic Theory" $3^{rd}$ edition, 1980.

The invention claimed is:

1. An implantable electrical heart stimulating device comprising:
    an electric energy storage unit;
    a first controlling electronics;
    a second controlling electronics;
    a piquita supporting structure comprising a proximal extremity, a distal extremity, an inner lumen with an outer surface;
    a plurality of electrodes comprising at least one electrode belonging to a group of active electrodes and/or to a group of passive electrodes;
    wherein the active electrodes are configured to inject electric current into the body cells surrounding the piquita supporting structure and;
    wherein the passive electrodes are configured to project electric fields into the body cells surrounding the piquita supporting structure while configured not to inject electric currents into the body cells surrounding the piquita supporting structure;
    wherein the first controlling electronics comprises first electronic circuits to select a subset of the plurality of electrodes to be operational;
    wherein the second controlling electronics comprises second electronic circuits to implement the selection from the first controlling electronics;
    wherein the electrically insulating layer on the passive electrodes acts as an insulator for DC current or low frequency cardiac signals, a opposed to the insulating layer to create a capacitor for capacitive coupling of the AC current;
    wherein the electrical field lines projected by the passive electrodes direct the path of moving electric charge in the body cells where the electric field lines are located;
    wherein the passive electrodes are configured to create an electric vector field in the body cells surrounding the piquita supporting structure, the electric vector field characterized by a magnitude and a direction, wherein the direction determines a plurality of field lines, along which the electric current is injected.

2. The implantable electric stimulating device of claim 1, further comprising an external programming unit, configured to provide instructions to the first controlling electronics and to the second controlling electronics, using wireless transmission, whereby a medical practitioner can adjust operation of the implantable electrical stimulating device.

3. The implantable electric stimulating device of claim 1, wherein the created electric vector field created by the at least one electrode of the group of passive electrodes is configured to force the path of the electric current injected by the active electrodes to move along a path and at a speed influenced by the created electric vector field lines.

4. The implantable electric stimulating device of claim 3, wherein the at least one electrode belonging to the group of passive electrodes are covered by an electrically insulating layer to prevent electric current from being injected into the body cells.

5. The implantable electric stimulating device of claim 1, further comprising a first binary digital addressing means to select each of the plurality of the electrodes on the body of the piquita supporting structure, wherein the first controlling electronics configured to cause the second controlling electronics to select a first subset of the at least one electrode of a group of active electrodes to be operational and a second subset of the at least one electrode of a group of passive electrodes to be operational.

6. The implantable electric stimulating device of claim 1, wherein the first and/or the second controlling electronics is/are configured to select a plurality of electric voltage or electric current values, wherein each of the at least one active electrode and at least one passive electrode has a voltage/current value each passive electrode and each active electrode a different voltage level a different current level same voltage level or the same current level.

7. The implantable electric stimulating device of claim 6, further comprising a plurality of voltage wires or current wires, each of the voltage wires or current wires to convey one voltage value and/or one current value.

8. The implantable electric stimulating device of claim 7, further comprising a second binary digital addressing means to select each voltage or current for electrical connection to a subset of the at least one of the group of active electrodes and/or the at least one of the group of passive electrodes.

9. The implantable electric stimulating device of claim 1, further comprising at least one digital serial bus to transfer digital binary information.

10. The implantable electric stimulating device of claim 9, wherein the digital serial bus is a digital part of a USB bus.

11. The implantable electric stimulating device of claim 1, wherein the piquita supporting structure is adapted to be anchored in a heart of an animal, including a human animal.

12. The implantable electric stimulating device of claim 1, wherein the first controlling electronics includes a microprocessor.

13. The implantable electric stimulating device of claim 1, wherein the active electrodes and the passive electrodes are randomly distributed on the body of the piquita supporting structure.

14. The implantable electric stimulating device of claim 1, wherein the at least one electrode belonging to the group of active electrodes and the at least one electrode belonging to the group of passive electrodes are symmetrically distributed on the body of the piquita supporting structure.

15. A method to activate at least one electrode in a multi-channel electrode array having a plurality of active electrodes and a plurality of passive electrodes, the method comprising:
    applying a first voltage on at least one of the plurality of passive electrodes, wherein the at least one passive electrode is configured to create an electric vector field in body cells surrounding the at least one passive electrode;

applying a second voltage on at least one of the plurality of active electrodes, wherein the at least one active electrode is configured to inject an electric charge in the body cells surrounding the at least one active electrode;

wherein the electrically insulating layer on the passive electrodes acts as an insulator for DC current or low frequency cardiac signals, as opposed to the insulating layer to create a capacitor for capacitive coupling of the AC current;

wherein the electrical field lines projected by the passive electrodes direct the path of moving electric charges in the body cells where the electric field lines are located;

wherein the electric vector field is configured to control the direction and speed of the electric charges injected in the body cells.

16. The method according to claim 15, further comprising simultaneously activating at least two of the plurality of passive electrodes using a different level of voltage on each of the two of the plurality of passive electrodes;

wherein at least two electrodes of the plurality of passive electrodes further increases the control of the shape of the electric vector field as compared with a single electrode of the plurality of passive electrodes.

17. The method according to claim 15, wherein the plurality of passive electrodes uses a monopolar configuration having a remote ground.

18. The method according to claim 15, wherein a first subset of electrodes of the multichannel electrode array are configured to be of a positive polarity and a second subset of electrodes are configured to be of a negative polarity;

wherein the first subset of electrodes and second subset of electrodes comprise different electrodes.

19. A non-transitory computer medium to provide instructions to an electrical stimulating device to control electrodes in a multichannel electrode array, wherein the electrodes belong to either an active group of electrodes or to a passive group of electrodes create a electric vector field;

wherein the electrodes of the active group of electrodes stimulate body cells and create the electric vector field and the electrodes of the passive group of electrodes determine the electric vector field.

wherein the electrically insulating layer on the passive electrodes acts as an insulator for DC current or for low frequency cardiac signals, as opposed to the insulating layer to create a capacitor for capacitive coupling of the AC current;

wherein the electric field lines projected by the passive electrodes direct the path of moving electric charges in the body cells where the electric field lines are located;

20. The non-transitory computer medium according to claim 19, wherein a first subset of electrodes of the multichannel electrode array are configured to be of a positive polarity and a second subset of electrodes are configured to be of a negative polarity;

wherein the first subset of electrodes and second subset of electrodes comprise different electrodes.

21. The non-transitory computer medium according to claim 19, further comprising instructions to display a window-style panel on a computer monitor, wherein the window-style panel displays and identifies with markers the position of the electrodes of the active group and the electrodes of the passive group, wherein a medical practitioner adjusts which electrodes are used and the voltage level at each electrode.

* * * * *